US010668172B2

(12) United States Patent
Chang et al.

(10) Patent No.: US 10,668,172 B2
(45) Date of Patent: *Jun. 2, 2020

(54) TREATMENT FOR EXPOSURE TO NERVE AGENT

(71) Applicant: Georgetown University, Washington, DC (

(56) References Cited

OTHER PUBLICATIONS

Clark, P. R. & Hersh, E. M. (1999). Cationic lipid-mediated gene transfer: current concepts. *Current Opinion in Molecular Therapeutics*, 1, 158-176.

Dimov, D. et al., (2012). Correlation between butyrylcholinesterase variants and sensitivity to soman toxicity. *Acta Biochimica Polonica*, 59, 313-316.

Ellman, G. et al., (1961). A new and rapid colorimetric determination of acetylcholinesterase activity. *Biochemical Pharmacology*, 7, 88-95.

Freedman, M. et al., (2009): Nanodelivery of MRI contrast agent enhances sensitivity of detection of lung cancer metastases. *Academic Radiology*, 16, 627-637.

Gunnell, D. et al., (2007). The global distribution of fatal pesticide self-poisoning: systematic review. *BMC Public Health*, 7, 357.

Haynes, B.F. et al., "Characterization of a Monoclonal Antibody (5E9) that Defines a Human Cell Surface Antigen of Cell Activation," *J. Immunol.* 127:347-352 (1981).

Hwang, S. H. et al., (2008). Tumor-targeting nanodelivery enhances the anticancer activity of novel quinazolinone analog. *Molecular Cancer Therapeutics*, 7(3), 1-10.

Jokanovic, M. (2009). Medical treatment of acute poisoning with organophosphorus and cabamate pesticides. *Toxicology Letters*, 190, 107-115.

Karnovsky, M. J. & Roots, L. (1964). A "direct-coloring" thiocholine method for cholinesterases. *Journal of Histochemistry & Cytochemistry*, 12, 219-221.

Kawabata, A. et al. (2001). In vivo evidence that protease-activated receptors 1 and 2 modulate gastrointestinal transit in the mouse. *British Journal of Pharmacology*, 133, 1213-1218.

Krejci et al., *The Journal of Biological Chemistry* 272:22840-22847 (1997).

Ledley, F. D. (1995). Nonviral gene therapy: the promise of genes an pharmaceutical products. *Human Gene Therapy*, 6, 1129-1144.

Li, H. et al., (2008). Lamellipodin proline rich peptides associated with native plasma butyrylcholinesterase tetramers. *Biochemical Journal*, 411, 425-432.

Li, B. et al., (2008). The butyrylcholinesterase knockout mouse as a model for human butyrylcholinesterase deficiency. *Journal of Pharmacology & Experimental Therapeutics*, 324, 1146-1154.

Lian, T. & Ho, R. J. (2001). Trends and developments in liposome drug delivery systems. *Journal of Pharmaceutical Sciences*, 90, 667-680.

Lockridge, O. et al., (1997). A single amino acid substitution, Gly117His, confers phosphotriesterase (organophosphorus acid anhydride hydrolase) activity on human butyrylcholinesterase. *Biochemistry*, 36, 786-795.

Marino, D. J. (2012). Absolute and relative organ weight trends in B6C3F1 mice. *Journal of Toxicology and Environmental Health, Part A: Current Issues*, 75(3), 148-169.

Masson, P. & Lockridge, O. (2010). Butyrylcholinesterase for protection from organophosphorus poisons: catalytic complexities and hysteretic behavior. *Archives of Biochemistry & Biophysics*, 494, 107-120.

McTiernan et al., "Brain cDNA clone for human chilinesterase," *Proc. Natl. Acad. Sci.* 84:6682-6685.

Millard, C. B. et al., (1995). Design and expression of organophosphorus acid anhydride hydrolase activity in human butyrylcholinesterase. *Biochemistry*, 34, 15925-15933.

Nachon, F. et al., (2011). X-ray crystallographic snapshots of reaction intermediates in the G117H mutant of human butyrylcholinesterase, a nerve agent target engineered into a catalytic bioscavenger. *Biochemical Journal*, 434, 73-82.

Paraoanu, L. E. et al., (2006). Exposure to diazinon alters in vitro retinogenesis: retinospheroid morphology, development of chicken retinal cell types, and gene expression. *Toxicological Sciences*, 89, 314-324.

Parikh, K. et al., (2011). Gene-delivered butyrylcholinesterase is prophylactic against the toxicity of chemical warfare nerve agents and organophosphorus compounds. *Journal of Pharmacology & Experimental Therapeutics*, 337, 92-101.

Pirollo, K. et al., (2000). Non-viral gene delivery for p53. *Current Opinion in Molecular Therapeutics*, 2, 168-175.

Pirollo, K. F. et al., (2008). Tumor-targeting nanocomplex delivery of novel tumor suppressor RB94 chemosensitizes bladder carcinoma cells in vitro and in vivo. *Clinical Cancer Research*, 14, 2190-2198.

Pirollo, K. F. et al., (2007). Materializing the Potential of siRNA via a Tumor-Targeting Nanodelivery System. *Cancer Research*, 67 (7), 2932-2937.

Rait, A. S. et al., (2002). Tumor-targeting, systemically delivered ASHER-2 chemosensitizes human breast cancer xenografts irresective of HER-2 levels. *Molecular Medicine*, 8, 475-486.

Rosenblum, K. et al., (2000). ERKI/II regulation by the muscarinic acetylcholine receptors in neurons. *Journal of Neuroscience*, 20, 977-985.

Saxena, A. et al., (2011). Pretreatment with human serum butyrylcholinesterase alone prevents cardiac abnormalities, seizures, and death in Gottingen minipigs exposed to sarin vapor. *Biochemical Pharmacology*, 82, 1984-1993.

Saxena, A. et al., Human serum butyrylcholinesterase: a bioscavenger for the protection of humans from organophosphorus exposure. RTO-MP-HFM-181. NATO/OTAN Monograph.

Senzer, N. et al., (2013). Phase I Study of a Systemically Delivered p53 Nanoparticle in Advanced Solid Tumors. *Molecular Therapy* 21:1096-1103; 922-923 (2013).

Trovaslet-Leroy, M. et al., (2011). Organophosphate hydrolases as catalytic bioscavengers of organophosphorus nerve agents. *Toxicology Letters*, 206, 14-23.

Wang, Y. et al., (2004). Resistance to organophosphorus agent toxicity in transgenic mice expressing the G117H mutant of human butyrylcholinesterase. *Toxicology & Applied Pharmacology*. 196, 356-366.

Xu, L. et al., (2002). Systemic tumor-targeted gene delivery by anti-transferrin receptor scFv-immunoliposomes. *Molecular Cancer Therapeutics*, 1, 337-346.

Yu, W. et al., (2004). Enhanced transfection efficiency of a systemically delivered tumor-targeting immunolipoplex by inclusion of a pH-sensitive histidylated oligolysine peptide. *Nucleic Acids Research*, 32, e48.

Pujals and Giral, "Proline-rich, ampipathic cell-penetrating peptides," Advanced Drug Delivery Reviews 60:473-484 (2008).

Ilarduya, et al. (2000) "Efficient gene transfer by transferrin lipoplexes in the presence of serum", Biochimica et Biophysica Acta (BBA)—Biomembranes, 1463(2): 333-42.

Rachou, et al. (1999) "Liposomes as a gene delivery system", Brazilian Journal of Medical and Biological Research, 32: 163-69.

Shim, et al. (2013) "Application of cationic liposomes for delivery of nucleic acids", Asian Journal of Pharmaceutical Sciences, 8: 72-80.

* cited by examiner

Subcloning into pSCMV:
EcoRI Digestion on 0.8% Agarose Gel, Ethidium Bromide Staining Lane 1 = pSCMV-mt BChE Lane 2 = pSCMV-ppro Lane 3 = pSCMV-wt BChE Marker = 1Kb Plus Marker

FIG. 7

Percent Supercoiled:

Lane 1 = pSCMV-wt BChE

Lane 2 = pSCMV-ppro

Lane 3 = pSCMV-mt BChE

Marker = λ Hind III

FIG. 8

TREATMENT FOR EXPOSURE TO NERVE AGENT

CROSS-REFERENCE TO RELATED APPLICATIONS

The present application is a continuation of U.S. application Ser. No. 14/208,187, filed Mar. 13, 2014, now U.S. Pat. No. 9,878,055, issued Jan. 30, 2018, which claims benefit of U.S. Provisional Application No. 61/783,001, filed Mar. 14, 2013, the disclosures of each of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Dec. 12, 2017, is named 2474-0021US2_SL.txt and is 1,093 bytes in size.

BACKGROUND OF THE INVENTION

Field of the Invention

The present application provides methods of preventing and treating the toxic effects of exposure to organophosphate agents. In embodiments, targeted cationic liposome complexes delivering nucleic acid molecules encoding butyrylcholinesterase and nucleic acid molecules encoding a polyproline rich sequence are administered. Suitably, the administration is via inhalation. Also provided are cationic liposome complexes and methods of making the complexes for such administration.

Background of the Invention

Organophosphate agents (OP) are commonly used as pesticides, insecticides and drugs for treatment of medical conditions such as glaucoma and Alzheimer's disease. Unfortunately, they have also been developed for use as nerve agents such as sarin, soman, VX, and tabun. These OP compounds are among the most toxic chemicals known. Exposure to even small amounts can be fatal. Death occurs from asphyxiation resulting from paralysis of the diaphragm and intracostal muscles, depression of the brain respiratory center, bronchospasm, convulsions and excessive salivation (reviewed in 1). The mechanism of OP poisoning is the phosphorylation of the serine hydroxyl group in the active site of Acetylcholinesterase (AchE) which leads to irreversible inactivation of the enzyme. AchE, which hydrolyzes Acetylcholine (Ach) at the synaptic space, is an essential enzyme in neurotransmission. Inactivation of AchE results in a rapid buildup of Ach subsequently producing PNS cholinergic hyperstimulation and death. In the CNS, cholinergic hyperexcitability increases neuronal firing triggering convulsions and acute neuronal cell death.

Although there are antidotal treatments for post-exposure use, they have shown limited efficacy, produce serious side effects, and do not prevent incapacitation (transient or permanent) or irreversible brain damage (1,2). Thus, prophylactic measures are being sought. One approach for counteracting OP toxicity is the use of a bioscavenger to sequester and neutralize these compounds. Of the bioscavengers tested, human serum butyrylcholinesterase (BChE) (also called pseudocholinesterase, or cholinesterase) appears to be the most suited for human use (3). BChE is a serine enzyme present in almost every tissue including plasma, brain, muscle, kidney, liver and lung (4). Human BChE (hBChE) (340 kDa) in serum is a globular tretrameric molecule with a $T_{1/2}$ of 11-14 days and is composed of four identical subunits and is protected from proteolysis through heavy glycosylation (5). The assembly of the individual subunits into the tetramer requires the presence of a polyproline rich peptide derived from lamellipodin (5) or from rat collagen tail (AChE Q subunit) (Bon paper, Krejci paper, Antamirano paper), or any other polyproline rich protein. BChE is naturally expressed at relatively high levels, 4 times that of the average gene (4). It also plays an important role in the degradation of numerous ester-containing drugs and is a natural bioscavenger of cholinesterase inhibitors, including potent OP nerve agents.

Each molecule of hBChE neutralizes one molecule of OP (6). It has been reported that pretreatment with recombinant human BChE and human serum BChE could protect animals (including rodents, guinea pigs, pigs and non-human primates) from up to 5 times $LD_{50}$ of nerve agents (6,7). The irreversible binding and inactivating function of BChE with a broad spectrum of OP poisons make it an ideal candidate for a prophylactic treatment against nerve agents. In addition to its use for a variety of wartime pre- and post-exposure scenarios, it also has potential use as a pretreatment for first responders reacting to intentional/accidental nerve gas release and as a post-exposure therapy for pesticide overexposure, cocaine overdose, or succinyl-choline-induced apnea (8).

It has been estimated that in a human, a BChE dose of 250 mg/70 kg is required to achieve efficient protection following a challenge with one $LD_{50}$ of OPs (3). However, the naturally occurring amount of this bioscavenger enzyme in blood (~8-72 mg/6 L) is too low to achieve adequate protection due to the stoichometric and irreversible binding of, and the interaction between, the OP and BChE; the unfavorable OP/BChE mass ratio; and the aging of the enzyme (4,9). Thus, it is critical to develop a means to significantly increase the level of BChE expression and amount in plasma. Toward this end, different strategies are being developed. The most straightforward is the direct injection of a large dose of highly purified natural hBChE to increase the amount in the bloodstream. This has proven to be successful for protection against lethal doses of soman and VX but, is not practical for battlefield use. Moreover, use of transgenic animals and cell culture has not been able to produce sufficient quantities of hBChE to be practical and feasible for use.

Derivation of BChE mutants capable of reactivating spontaneously (making them available to bind and deactivate additional molecules of OP) is another approach being employed with some success. BChE was shown to gain OP hydrolase activity and increased reactivation when a Histidine was substituted for Glycine at position 117 (G117H) (10,11). This mutant is efficient at hydrolyzing the acetylcholinesterase inhibitor echothiophate and can also efficiently hydrolyze the nerve agents sarin and VX (9). More importantly, transgenic mice expressing the G117H mutant are resistant to OP (12). Although upwards of 60 BChE mutants have been produced, the G117H remains one of the most efficient and studied to date (9). However, as yet, no means of efficiently delivering or producing for extended periods of time in the body after administration, a BChE or tetrameric form of active mtBChE via non-invasive routes, has been developed.

There is, therefore, an urgent need to develop technologies and methods to deliver BChE for prevention and treatment of exposure to OP agents. The present invention fulfills these needs by providing cationic-liposome-based drug delivery systems for such treatment and/or prevention.

BRIEF SUMMARY OF THE INVENTION

In one embodiment, methods of treating or preventing toxicity associated with exposure to an organophosphate agent in a mammal are provided. Such methods suitably comprise administering to the mammal a cationic liposome complex, wherein the cationic liposome complex comprises a cationic liposome, a ligand directly complexed with, but not chemically conjugated to, the cationic liposome, a nucleic acid molecule encoding butyrylcholinesterase (BChE) associated with the cationic liposome, and a nucleic acid molecule encoding a polyproline rich peptide associated with the cationic liposome.

In embodiments, the complex is administered via a route selected from the group consisting of intranasal administration, intravenous administration, oral administration, sublingual administration, intramuscular administration, intralesional administration, intradermal administration, transdermal administration, intraocular administration, intraperitoneal administration, percutaneous administration, aerosol administration, intraorgan administration, intracerebral administration, topical administration, subcutaneous administration, endoscopic administration, slow release implant, administration via an osmotic or mechanical pump and administration via inhalation.

Suitably, the ligand is transferrin, an antibody and an antibody fragment, including a single chain Fv antibody fragment, such as an anti-transferrin receptor single chain Fv (TfRscFv).

In further embodiments, the ligand-targeted cationic liposome further comprises a peptide comprising a K[K(H)KKK]5-K(H)KKC (HoKC) (SEQ ID NO: 1) peptide associated with the cationic liposome.

Suitably, the nucleic acid molecule encoding BChE is contained in a first plasmid and the nucleic acid molecule encoding the polyproline rich peptide is contained in a second plasmid. In embodiments, the nucleic acid molecule encoding BChE is contained in a first plasmid construct, comprising, from 5' to 3': (a) at least one human adenovirus enhancer sequence; (b) a cytomegalovirus (CMV) promoter; (c) a multiple cloning site; (d) the nucleic acid molecule encoding BChE; and (e) an SV 40 poly A sequence, wherein the 3' end of the plasmid construct does not comprise adenovirus map units 9-16 when compared to a wild-type adenovirus. In embodiments, the nucleic acid molecule encoding the polyproline rich peptide is contained in a second plasmid construct, comprising, from 5' to 3': (a) at least one human adenovirus enhancer sequence; (b) a cytomegalovirus (CMV) promoter; (c) a multiple cloning site; (d) the nucleic acid molecule encoding the polyproline rich peptide; and (e) an SV 40 poly A sequence, wherein the 3' end of the plasmid construct does not comprise adenovirus map units 9-16 when compared to a wild-type adenovirus.

Alternatively the nucleic acid molecule encoding BChE, and the nucleic acid molecule encoding the polyproline rich peptide, are in the same construct, but the nucleic acid molecule encoding BChE is placed downstream from the high expression promoter disclosed in U.S. Published Patent Application No. 2007/0065432, while the nucleic acid molecule encoding the polyproline rich peptide is placed downstream of a standard promoter such as RSV or CMV Suitably, the BChE is a mutant version of BChE, including the mutant version of BChE is a G117H mutant.

In exemplary embodiments, the cationic liposome comprises a mixture of one or more cationic lipids and one or more neutral or helper lipids. Suitably the ligand and the cationic liposome are present at a ratio in the range of about 1:1 to about 1:100 (w:w), for example at a ratio in the range of about 1:10 to about 1:50 (w:w), or at a ratio in the range of about 1:20 to about 1:40 (w:w).

In embodiments, the cationic liposome comprises a mixture of dioleoyltrimethylammonium phosphate with dioleoylphosphatidylethanolamine and cholesterol; a mixture of dioleoyltrimethylammonium phosphate with cholesterol, a mixture of dimethyldioctadecylammonium bromide with dioleoylphosphatidylethanolamine and cholesterol, a mixture of dimethyldioctadecylammonium bromide with dioleoylphosphatidylethanolamine, a mixture of dimethyldioctadecylammonium bromide with cholesterol, or a mixture of dioleoyltrimethylammonium phosphate with dioleoylphosphatidylethanolamine.

Suitably, the nucleic acid molecules in the cationic immunoliposome complex are present at a molar ratio of about 10:1 to about 1:10 (moles nucleic acid molecule encoding butyrylcholinesterase (BChE):moles nucleic acid molecule encoding a polyproline rich peptide), or the nucleic acid molecules are present at a molar ratio of about 5:1 to about 1:5 (moles nucleic acid molecule encoding butyrylcholinesterase (BChE):moles nucleic acid molecule encoding a polyproline rich peptide), or more suitably the nucleic acid molecules are present at a molar ratio of about 4:1 (moles nucleic acid molecule encoding butyrylcholinesterase (BChE):moles nucleic acid molecule encoding a polyproline rich peptide), or more suitably the nucleic acid molecules are present at a molar ratio of about 2:1 (moles nucleic acid molecule encoding butyrylcholinesterase (BChE):moles nucleic acid molecule encoding a polyproline rich peptide) or more suitably the nucleic acid molecules are present at a molar ratio of about 1:1 (moles nucleic acid molecule encoding butyrylcholinesterase (BChE):moles nucleic acid molecule encoding a polyproline rich peptide).

In embodiments, the total amount of nucleic acid molecules is present at a weight ratio of between about 1:1 to about 1:40 (μg nucleic acid:μg liposome), or about 1:5 to about 1:20 (μg total nucleic acid:μg liposome), or more suitably the total amount of nucleic acid molecules is present at a weight ratio about 1:10 (μg total nucleic acid: μg liposome).

Suitably, the complex is administered so as to treat toxicity associated with exposure to at least $1\times LD_{50}$ of the organophosphate agent, more suitably so as to treat toxicity associated with exposure to up to $10\times LD_{50}$ of the organophosphate agent. In embodiments, the complex is administered so as to prevent toxicity associated with exposure to at least $1\times LD_{50}$ of the organophosphate agent, more suitably exposure to up to 10×LD50 of the organophosphate agent.

In embodiments, the complex is administered immediately before or after exposure to the organophosphate agent. In further embodiments, the complex is administered at least 6 hours prior to potential exposure to the organophosphate agent. Suitably, the complex is administered at least once a week prior to potential exposure to the organophosphate agent.

Suitably, the mammal is a human.

Also provided are methods of treating toxicity associated with exposure to an organophosphate agent in a human. Such methods suitably comprise administering intranasally or via aerosol inhalation to the human a cationic liposome complex, wherein the cationic liposome complex comprises a cationic liposome, an anti-transferrin receptor single chain Fv (TfRscFv) directly complexed with, but not chemically conjugated to, the cationic liposome, a nucleic acid molecule encoding butyrylcholinesterase (BChE) contained in a first plasmid associated with the cationic liposome, and a nucleic acid molecule encoding a polyproline rich peptide contained in a second plasmid associated with the cationic liposome. Suitably the TfRscFv and the cationic liposome are present at a ratio in the range of about 1:20 to about 1:40 (w:w) and the nucleic molecules are present at a ratio of about 1:5 to about 1:20 (µg nucleic acid:µg liposome). Suitably, the nucleic acid molecules in the cationic immunoliposome complex are present at a molar ratio of about 10:1 to about 1:10 (moles nucleic acid molecule encoding butyrylcholinesterase (BChE): moles nucleic acid molecule encoding a polyproline rich peptide), or the nucleic acid molecules are present at a molar ratio of about 5:1 to about 1:5 (moles nucleic acid molecule encoding butyrylcholinesterase (BChE):moles nucleic acid molecule encoding a polyproline rich peptide), or more suitably the nucleic acid molecules are present at a molar ratio of about 4:1 (moles nucleic acid molecule encoding butyrylcholinesterase (BChE):moles nucleic acid molecule encoding a polyproline rich peptide). or more suitably the nucleic acid molecules are present at a molar ratio of about 2:1 (moles nucleic acid molecule encoding butyrylcholinesterase (BChE):moles nucleic acid molecule encoding a polyproline rich peptide) or more suitably the nucleic acid molecules are present at a molar ratio of about 1:1 (moles nucleic acid molecule encoding butyrylcholinesterase (BChE):moles nucleic acid molecule encoding a polyproline rich peptide). In embodiments, the complex is administered so as to treat toxicity associated with exposure to at least 1×LD50 of the organophosphate agent.

Also provided are methods of preventing toxicity associated with exposure to an organophosphate agent in a human. Such methods suitably comprise administering intranasally or via aerosol inhalation to the human a cationic liposome complex, wherein the cationic liposome complex comprises a cationic liposome, an anti-transferrin receptor single chain Fv (TfRscFv) directly complexed with, but not chemically conjugated to, the cationic liposome, a nucleic acid molecule encoding butyrylcholinesterase (BChE) contained in a first plasmid associated with the cationic liposome, and a nucleic acid molecule encoding a polyproline rich peptide contained in a second plasmid associated with the cationic liposome. Suitably the TfRscFv and the cationic liposome are present at a ratio in the range of about 1:20 to about 1:40 (w:w) and the nucleic molecules are present at a ratio of about 1:5 to about 1:20 (µg nucleic acid:µg liposome). Suitably, the nucleic acid molecules in the cationic immunoliposome complex are present at a molar ratio of about 10:1 to about 1:10 (moles nucleic acid molecule encoding butyrylcholinesterase (BChE): moles nucleic acid molecule encoding a polyproline rich peptide), or the nucleic acid molecules are present at a molar ratio of about 5:1 to about 1:5 (moles nucleic acid molecule encoding butyrylcholinesterase (BChE):moles nucleic acid molecule encoding a polyproline rich peptide), or more suitably the nucleic acid molecules are present at a molar ratio of about 4:1 (moles nucleic acid molecule encoding butyrylcholinesterase (BChE):moles nucleic acid molecule encoding a polyproline rich peptide) or more suitably the nucleic acid molecules are present at a molar ratio of about 2:1 (moles nucleic acid molecule encoding butyrylcholinesterase (BChE):moles nucleic acid molecule encoding a polyproline rich peptide) or more suitably the nucleic acid molecules are present at a molar ratio of about 1:1 (moles nucleic acid molecule encoding butyrylcholinesterase (BChE):moles nucleic acid molecule encoding a polyproline rich peptide). In embodiments, the complex is administered so as to prevent toxicity associated with exposure to at least 1×LD50 of the organophosphate agent.

Also provided are methods of delivering butyrylcholinesterase (BChE) to the bloodstream of a mammal. Such methods suitably comprise administering intranasally or via aerosol inhalation to the mammal a cationic liposome complex, wherein the cationic liposome complex comprises a cationic liposome, an anti-transferrin receptor single chain Fv (TfRscFv) directly complexed with, but not chemically conjugated to, the cationic liposome, a nucleic acid molecule encoding butyrylcholinesterase (BChE) contained in a first plasmid associated with the cationic liposome, and a nucleic acid molecule encoding a polyproline rich peptide contained in a second plasmid associated with the cationic liposome. Suitably the TfRscFv and the cationic liposome are present at a ratio in the range of about 1:20 to about 1:40 (w:w) and the nucleic molecules are present at a ratio of about 1:5 to about 1:20 (µg nucleic acid:µg liposome). Suitably, the nucleic acid molecules in the cationic immunoliposome complex are present at a molar ratio of about 10:1 to about 1:10 (moles nucleic acid molecule encoding butyrylcholinesterase (BChE):moles nucleic acid molecule encoding a polyproline rich peptide), or the nucleic acid molecules are present at a molar ratio of about 5:1 to about 1:5 (moles nucleic acid molecule encoding butyrylcholinesterase (BChE):moles nucleic acid molecule encoding a polyproline rich peptide), or more suitably the nucleic acid molecules are present at a molar ratio of about 4:1 (moles nucleic acid molecule encoding butyrylcholinesterase (BChE):moles nucleic acid molecule encoding a polyproline rich peptide) or more suitably the nucleic acid molecules are present at a molar ratio of about 2:1 (moles nucleic acid molecule encoding butyrylcholinesterase (BChE):moles nucleic acid molecule encoding a polyproline rich peptide) or more suitably the nucleic acid molecules are present at a molar ratio of about 1:1 (moles nucleic acid molecule encoding butyrylcholinesterase (BChE): moles nucleic acid molecule encoding a polyproline rich peptide). In embodiments, the complex is administered so as to result in an amount of BChE in the bloodstream of the human of at least 250 mg/70 kg (weight of BChE/weight of the human).

Alternatively the nucleic acid molecule encoding BChE, and the nucleic acid molecule encoding the polyproline rich peptide, are in the same construct, but the nucleic acid molecule encoding BChE is placed downstream from the high expression promoter disclosed in U.S. Published Patent Application No. 2007/0065432 (incorporated by reference herein in its entirety), while the nucleic acid molecule encoding the polyproline rich peptide is placed downstream of a standard promoter such as RSV or CMV

BRIEF DESCRIPTION OF THE DRAWINGS/FIGURES

FIG. 7 shows the results of the subcloning of wt-BChE, mt-BChE and ppro genes into the pSCMV vector.

FIG. 8 shows the percent supercoiled of wt-BChE, mt-BChE and ppro genes in pSCMV vectors.

DETAILED DESCRIPTION OF THE INVENTION

Figure 1:
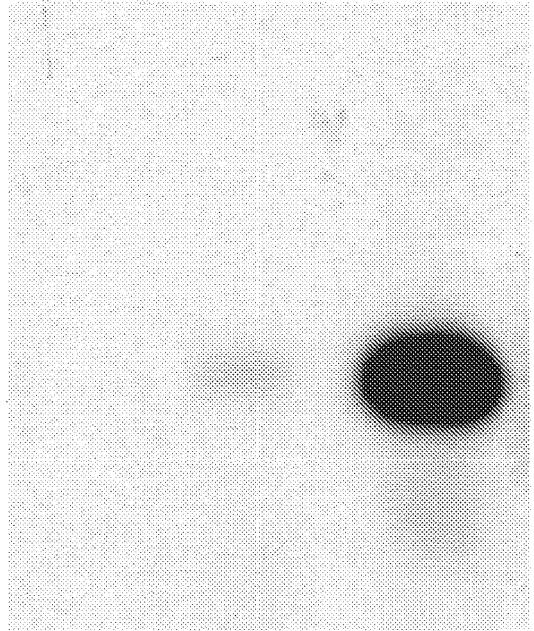
FIG. 1 shows the presence of transgene expression in metastatic tumors from targeted catonic immunoliposome delivery.

The terms "complex," "nanocomplex," "liposome complex" and "nanoliposome" are used interchangeably throughout to refer to the cationic liposomes described herein. Exemplary cationic liposomes for use in the practice of the present invention and methods of production thereof are disclosed in U.S. Published Patent Application Nos. 2003/0044407 and 2007/0065499, the disclosures of each of which are incorporated by reference herein in their entireties.

As used herein the term "about" refers to the recited value, as well as values within 10% of the recited value. For example, "about 100 nm" includes the values of 90 nm to 110 nm, including values in between this range.

As used herein the term "ligand" refers to any suitable targeting moiety that can be either chemically conjugated to, or directly associated/complexed with, but not chemically conjugated to, the cationic liposomes. Exemplary ligands for use in the practice of the present invention include, but are not limited to, proteins (e.g., transferrin or folate), peptides (e.g., L-37 pA), antibodies, antibody fragments (including Fab' fragments and single chain Fv fragments) and sugars (e.g., galactose), as well as other targeting molecules.

Exemplary methods and compositions in which the complexes in accordance with embodiments of this invention are made by a simple and efficient non-chemical conjugation are disclosed in U.S. Published Patent Application Nos. 2003/0044407 and 2007/0065499. Exemplary methods and compositions in which the complexes in accordance with embodiments of this invention are made via chemical conjugation are disclosed in U.S. Pat. No. 7,479,276. The disclosures of each of these patents and patent applications are incorporated by reference herein in their entireties.

In exemplary embodiments, a whole antibody or an antibody fragment can be used as the ligand to make the complexes of this invention. In a suitable embodiment, an antibody fragment is used, including Fab fragments and single chain Fv fragments (scFv) of an antibody. One suitable antibody is an anti-Transferrin receptor (anti-TfR) monoclonal antibody, and a suitable antibody fragment is an scFv based on an anti-TfR monoclonal antibody. A suitable anti-TfR monoclonal antibody is 5E9 (see, e.g., Hayes, B. F., et al., "Characterization of a Monoclonal Antibody (5E9) that Defines a Human Cell Surface Antigen of Cell Activation," *J. Immunol.* 127:347-352 (1981); Batra, J. K., et al., "Single-chain Immunotoxins Directed at the Human Transferrin Receptor Containing Pseudomonas Exotoxin A or Diphtheria Toxin: Anti-TFR(Fv)-PE40 and DT388-Anti-TFR(Fv)," *Mol. Cell. Biol.* 11:2200-2205 (1991) (the disclosures of which are incorporated herein by reference). An scFv based on the full anti-TfR monoclonal antibody contains the complete antibody binding site for the epitope of the TfR recognized by this MAb as a single polypeptide chain of approximate molecular weight 26,000. An scFv is formed by connecting the component VH and VL variable domains from the heavy and light chains, respectively, with an appropriately designed peptide, which bridges the C-terminus of the first variable region and N-terminus of the second, ordered as either VH-peptide-VL or VL-peptide-VH. Additional ligands, such as those described throughout, can also be used in the practice of the present invention.

In one embodiment, a cysteine moiety is added to the C-terminus of the scFv. Although not wishing to be bound by theory, it is believed that the cysteine, which provides a free sulfhydryl group, may enhance the formation of the complex between the antibody and the liposome in both the chemically conjugated and non-chemically conjugated embodiments. With or without the cysteine, the protein can be expressed in *E. coli* inclusion bodies and then refolded to produce the antibody fragment in active form.

Unless it is desired to use a sterically stabilized liposome in the formation of the complexes, a first step in making exemplary non-chemically conjugated complexes of the present invention comprise mixing a cationic liposome or combination of liposomes with the antibody or antibody fragment of choice. A wide variety of cationic liposomes are useful in the preparation of the complexes of this invention. Published PCT application WO99/25320 (the disclosure of which is incorporated by reference herein in its entirety) describes the preparation of several cationic liposomes. Examples of suitable liposomes include phosphatidylcholine (PC), phosphatidylserine (PS) and those that comprise a mixture dioleoyltrimethylammonium phosphate (DOTAP) and dioleoylphosphatidylethanolamine (DOPE), a DOTAP and DOPE and/or cholesterol (chol); a mixture of dimethyldioctadecylammonium bromide (DDAB) and DOPE and/or chol, or a mixture of DDAB and DOPE. The ratio of the lipids can be varied to optimize the efficiency of uptake of the therapeutic molecule for the specific target cell type. The liposome can comprise a mixture of one or more cationic lipids and one or more neutral or helper lipids. A desirable ratio of cationic lipid(s) to neutral or helper lipid(s) is about 1:(0.5-3), preferably 1:(1-2) (molar ratio).

Suitable ligands, for example, proteins/peptides, antibody or antibody fragments, are those that will bind to the surface of the target cell, and preferably to a receptor that is differentially expressed on the target cell. The ligands are mixed with the cationic liposome or polymer at room temperature and at a ligand (e.g., protein):lipid ratio (weight: weight) in the range of about 1:10 to about 1:50, suitably about 1:20 to about 1:40 (w:w).

The ligand (e.g., the protein/peptide, antibody or antibody fragment) and the liposome are allowed to incubate at room temperature for a short period of time, typically for about 10-15 minutes, then the mixture is mixed with a therapeutic or diagnostic agent of choice. Examples of therapeutic molecules or agents which can be complexed to the liposome complexes include genes, high molecular weight DNA (genomic DNA), plasmid DNA, antisense oligonucleotides, peptides, ribozymes, nucleic acids (including siRNA, miRNA and antisense), small molecules, viral particles, immunomodulating agents, contrast agents for imaging, proteins and chemical agents.

The ligand (e.g., the protein/peptide, antibody or antibody fragment) and liposome combination is mixed with the therapeutic agent at a ratio in the range of about 0.5:1 to about 1:40 (µg of agent:nmol of total lipid), suitably about 1:10 to 1:20 (µg of agent:nmole of total lipid) and incubated at room temperature for a short period of time, typically about 10 to 15 minutes. For use in vivo, 50% dextrose or 50% sucrose is added to a final concentration of 5-20% (V:V) and mixed by gentle inversion for 5-10 seconds, or for larger volumes rotated at 20-30 RPM for 1-2 minutes The size of the liposome complex is typically within the range of about 50-500 nm as measured by dynamic light scattering using a Malvern ZETASIZER® 3000 or a Malvern ZETASIZER® NANO-ZS. See U.S. Published Patent Application No. 2003/0044407 and U.S. patent application Ser. No. 11/520,796, the disclosures of which are incorporated by reference herein in their entireties.

In one embodiment of this invention, the liposome used to form the complex is a sterically stabilized liposome. Sterically stabilized liposomes are liposomes into which a hydrophilic polymer, such as PEG, poly(2-ethylacrylic acid), or poly(n-isopropylacrylamide (PNIPAM) has been integrated. Such modified liposomes can be particularly useful when complexed with therapeutic agents, as they typically are not cleared from the bloodstream by the reticuloendothelial system as quickly as are comparable liposomes that have not been so modified. To make a sterically stabilized liposome complex of the present invention, the order of mixing the antibody or antibody fragment, the liposome and the therapeutic or diagnostic agent is reversed from the order set forth above. In a first step, a cationic liposome as described above is first mixed with a therapeutic agent as described above at a ratio in the range of about 0.5:1 to about 1:40 (µg of agent:nmol of lipid), suitably about 1:10 to 1:20 (µg of agent:nmole of lipid). To this lipoplex is added a solution of a PEG polymer in a physiologically acceptable buffer at a ratio of about 0.1:100 (nmol of PEG:nmol of liposome), suitably, about 0.5:50, for example, about 1:40 (nmol of PEG:nmol of liposome). The resultant solution is incubated at room temperature for a time sufficient to allow the polymer to integrate into the liposome complex. The ligand (e.g., protein/peptide, antibody or antibody fragment) then is mixed with the stabilized liposome complex at room temperature and at a ligand (e.g., protein):lipid ratio in the range of about 1:5 to about 1:40 (w:w). For use in vivo, 50% dextrose or 50% sucrose is added to a final concentration of 5-20% (V:V) and mixed by gentle inversion for 5-10 seconds, or for larger volumes rotated at 20-30 RPM for 1-2 minutes.

The liposomal complexes prepared in accordance with the present invention can be formulated as a pharmacologically acceptable formulation for in vivo administration. The complexes can be combined with a pharmacologically compatible vehicle or carrier. The compositions can be formulated, for example, for intravenous administration to a mammal, for example a human patient to be benefited by administration of the therapeutic molecule, or other payload, in the complex. The complexes are of an appropriate size so that they are distributed throughout the body following i.v. administration. Alternatively, the complexes can be delivered via other routes of administration, such as intratumoral (IT), intralesional (IL), aerosol, percutaneous, oral, endoscopic, topical, intramuscular (IM), intradermal (ID), intraocular (IO), intraperitoneal (IP), transdermal (TD), intranasal (IN), intracereberal (IC), intraorgan (e.g. intrahepatic), slow release implant, or subcutaneous administration, or via administration using an osmotic or mechanical pump or via inhalation. Preparation of formulations for delivery via such methods, and delivery using such methods, are well known in the art.

The complexes can be optimized for target cell type through the choice and ratio of lipids, the ratio of ligand (e.g., protein/peptide, antibody or antibody fragment) to liposome, the ratio of ligand and liposome to the therapeutic agent, and the choice of ligand and therapeutic agent.

The complexes made in accordance with the methods of this invention can be provided in the form of kits for use in the systemic delivery of a nucleic acid, therapeutic molecule, or other payload by the complex. Suitable kits can comprise, in separate, suitable containers, the liposome, the ligand (e.g., protein/peptide, antibody or antibody fragment), and the nucleic acid, the therapeutic or diagnostic agent. The components can be mixed under sterile conditions in the appropriate order and administered to a patient within a reasonable period of time, generally from about 30 minutes to about 24 hours, after preparation. The kit components preferably are provided as solutions or as dried powders. Components provided in solution form, preferably are formulated in sterile water-for-injection, along with appropriate buffers, osmolarity control agents, etc. The complete complex can also be formulated as a dried powder (lyophilized) (see, e.g., U.S. Published Patent Application No. 2005/0002998, the disclosure of which is incorporated by reference herein in its entirety).

As discussed throughout U.S. Published Patent Application Nos. 2003/0044407 and 2007/0065499, the disclosures of which are incorporated herein by reference, the cationic liposome complexes described throughout have successfully delivered various therapeutic and diagnostic agents to tumor cells, via targeting using the anti-transferring single chain antibody fragment (TfRscFv). Specifically, nucleic acid molecules, e.g., antisense and siRNA, as well as plasmid DNA (such as p53 and RB94), have been successfully delivered using the liposome complexes of the present invention (see U.S. Published Patent Application Nos. 2003/0044407 and 2007/0065499).

Cationic Liposome Complexes for Prevention or Treatment Toxicity Associated with Organophosphate Agents As described above, the use of BChE as an OP bioscavenger can be used as a prophylactic agent. However, the inability to produce and rapidly deliver sufficient quantities when needed is a major hurdle to implementation of these use of this compound. Therefore, it is critical to develop a means to increase expression of BChE in the circulation and in other tissues such as lung, liver and brain.

Recombinant human BChE has been produced using mammalian cell cultures, transgenic goats, plants and silk worm larvae (23). Although this recombinant BChE proved to be successful for protection against lethal doses of soman and VX, production through these methods is not practical given the high cost of producing large quantities of GMP material and potential stability and safety issues. Thus, other approaches are being explored. Parikh and colleagues (23) have used adenovirus to deliver mouse BChE. They found that this intravenously administered Ad-MoBChE was able to protect mice from multi $LD_{50}$ doses of OPs VX and echothiophate at a level equivalent to a multimilligram injection of pure BChE. Although elevated amounts of BChE were produced, the levels achieved did not translate to production of the amount of BChE required to protect a human, estimated at a minimum to be 250 mg/70 kg. One possible reason for this is that the BChE protein produced in the mice was not the tetrameric form, but was primarily dimers (85%) which are eliminated rapidly in mammals. The therapeutic potential of BChE is dependent on its ability to remain in circulation for an extended period of time. This stability is in turn dependent on maintaining the tetrameric structure. Moreover, the use of viral vectors for delivery systems have potential immunogenicity problems and drawbacks associated with the necessity for intravenous administration and repeat administration.

Thus, other methods need to be developed that do not have immunogenicity issues associated with repeat administration; can be easily self administered in the field; and, more importantly, can result in significantly high levels of expression of the preferred tetrameric form of BChE with increased time in circulation. The liposome approach described herein offers a number of advantages over viral methodologies for gene delivery including lack of immunogenicity (24). Cationic liposomes have proven to be safe and efficient for in vivo gene delivery (25,26). More than 110 clinical trials using cationic liposomes for DNA delivery, including 85 in the US, have been approved (27) and at least 6 liposome-based products are on the market (28).

As described herein, targeted liposome complexes carrying both a plasmid encoding BChE, including mutant forms such as the more active G117H mutant form (see e.g., Reference 11, the disclosure of which is incorporated by reference here in its entirety) of BChE, and a plasmid encoding the gene for a proline rich peptide (such as rQ45) to facilitate tetramerization, are provided. When administered at the threat of potential OP exposure, the genes are efficiently delivered to various tissues including lung, brain and liver, with subsequent high levels of expression of fresh, OP resistant, tetrameric hBChE, being continuously produced and present in the circulation for an extended period of time (e.g., 1 Day to 14 days or longer). As described herein, such methods are suitably a prophylactic measure designed to protect if there is a possibility of nerve gas exposure, and as a post-exposure therapeutic OP countermeasure. It has been established that genetic variants of human BChE which can increase the sensitivity of individuals to OPs are common (29,30). The methods described herein can provide high levels of exogenous, active BChE to override this inherent genetic sensitivity and protect both this subset and the general population.

Preparation of Liposome Complexes

In an exemplary embodiment, the present invention provides methods of preparing a ligand-targeted (e.g., protein/peptide, antibody- or antibody fragment-targeted) cationic liposome complex. In suitable embodiments, such methods comprise preparing a ligand (e.g., protein/peptide, antibody or antibody fragment), and mixing the ligand with a cationic liposome to form a ligand-targeted cationic liposome, wherein the ligand is directly associated/complexed with, but is not chemically conjugated to, the cationic liposome. The ligand-targeted cationic liposome is then mixed with one or more nucleic acid molecules.

In embodiments the nucleic acid molecules comprise a nucleic acid molecule encoding butyrylcholinesterase (BChE) associated with the cationic liposome and a nucleic acid molecule encoding a polyproline rich peptide, associated with the cationic liposome, to form the ligand-targeted cationic liposome complex. Sequences of nucleic acid molecules encoding BChE are readily known in the art or otherwise described herein. See, e.g., McTiernan, et al., "Brain cDNA clone for human cholinesterase," *Proc. Natl. Acad. Sci.* 84:6682-6686, FIG. 2, the disclosure of which is incorporated by reference herein in its entirety for all purposes.

Sequences of nucleic acid molecules encoding a polyproline rich peptide are described herein or otherwise known in the art. An exemplary nucleic acid encoding the amino terminal 45 residues (rQ45) of the rat collagen tail, including the polyproline rich peptide domain (also called proline-rich attachment domain (PRAD)) are disclosed in, for example, Altamirano and Lockridge, *Chemico-Biological Interactions* 119-120:53-60 (1999) (see page 57, section 2.9); Krejci et al., *The Journal of Biological Chemistry* 272:22840-22847 (1997) (see page 22842, FIG. 1); and Bon et al., The *Journal of Biological Chemistry* 272:3016-3021 (1997) (see section bridging pages 3016-3017) (the disclosures of each of which are incorporated by reference herein in their entireties).

In another exemplary embodiment, the present invention provides methods of preparing a ligand-targeted (e.g., protein/peptide, antibody- or antibody fragment-targeted) cationic liposome complex. In suitable embodiments, such methods comprise preparing a ligand (e.g., protein/peptide, antibody or antibody fragment), and mixing the ligand with a cationic liposome to form a ligand-targeted cationic liposome, wherein the ligand is directly complexed with the cationic liposome via chemical conjugation. The ligand-targeted cationic liposome is then mixed with one or more nucleic acid molecules as described herein, to form the ligand-targeted cationic liposome complex.

As described herein, nucleic acid molecules are associated with the cationic liposome, which includes the nucleic acid molecules being suitably encapsulated, contained or complexed/associated with the liposome complexes of the present invention by simply mixing the one or more nucleic acid molecules with the liposomes during processing. Suitable ratios of nucleic acid molecules:liposome complexes are readily determined by the ordinarily skilled artisan and described herein.

In embodiments, the nucleic acid molecule encoding BChE is contained in a first plasmid and the nucleic acid molecule encoding the polyproline rich peptide is contained in a second plasmid. That is, the proteins are encoded from different plasmids. However, in further embodiments, the proteins can be encoded from the same plasmid, i.e., both genes contained in the same plasmid.

Suitably, the two distinct plasmids utilized to encode the nucleic acid molecules are the same, with the exception of the gene that they encode. In suitable embodiments the nucleic acid molecule encoding BChE, and the nucleic acid molecule encoding the polyproline rich peptide, are placed downstream from a nucleic acid promoter, for example, a promoter as described in U.S. Published patent application No. 2007/0065432, the disclosure of which is incorporated by reference herein in its entirety. Suitably, the nucleic acid molecules are placed in a plasmid construct, comprising, from 5' to 3': (a) at least one human adenovirus enhancer sequence; (b) a cytomegalovirus (CMV) promoter; (c) a multiple cloning site; (d) the nucleic acid molecule encoding BChE of the nucleic acid molecule encoding the polyproline rich peptide; and (e) an SV 40 poly A sequence, wherein the 3' end of the plasmid construct does not comprise adenovirus map units 9-16 when compared to a wild-type adenovirus. See FIG. 3 of U.S. Published Patent Application No. 2007/0065432, which is specifically incorporated by reference herein.

Alternatively the nucleic acid molecule encoding BChE, and the nucleic acid molecule encoding the polyproline rich peptide, are in the same construct, but the nucleic acid molecule encoding BChE is placed downstream from the high expression promoter disclosed in U.S. Published Patent Application No. 2007/0065432, while the nucleic acid molecule encoding the polyproline rich peptide is placed downstream of a standard promoter such as RSV or CMV.

In exemplary embodiments, the nucleic acids are present at a molar ratio of about 10:01 to about 0.1:10 (moles nucleic acid molecule encoding butyrylcholinesterase (BChE): moles nucleic acid molecule encoding a polyproline rich peptide). In exemplary embodiments, the nucleic acids are present at a molar ratio of about 10:1 to about 1:10 (moles nucleic acid molecule encoding butyrylcholinesterase (BChE):moles nucleic acid molecule encoding a polyproline rich peptide). For example, the nucleic acid molecules encoding butyrylcholinesterase (BChE) and the nucleic acid molecule encoding a polyproline rich peptide are present in the liposomes at a molar ratio in the range of about 10:1 to about 1:10, or about 5:1 to about 1:5, or more suitably about 4:1 (moles nucleic acid molecule encoding butyrylcholinesterase (BChE):moles nucleic acid molecule encoding a polyproline rich peptide), or more suitably the nucleic acid molecules are present at a molar ratio of about 2:1 (moles nucleic acid molecule encoding butyrylcholinesterase (BChE):moles nucleic acid molecule encoding a polyproline rich peptide) or more suitably the nucleic acid molecules are present at a molar ratio of about 1:1 (moles nucleic acid molecule encoding butyrylcholinesterase (BChE):moles nucleic acid molecule encoding a polyproline rich peptide). Additional molar ratios outside of these ranges can also be used.

Suitably, the molar ratio of nucleic acid molecules to liposome complex is in the range of about 0.5:1 to about 1:40 (μg total nucleic acid:μg liposome), or about 1:1 to about 1:40 (μg total nucleic acid:μg liposome), suitably about 1:5 to about 1:20 (μg total nucleic acid:μg liposome), more suitably about 1:10 (μg total nucleic acid:μg liposome). As utilized herein, the molar ratio of nucleic acid molecules to liposome complex includes both "populations" of nucleic acids, i.e., the total amount of nucleic acid includes one or more nucleic acid molecules encoding BChE, and one or more nucleic acid molecules encoding a polyproline rich peptide.

As described throughout, examples of desirable cationic liposomes for delivery of nucleic acid molecules include those that comprise a mixture of dioleoyltrimethylammonium phosphate (DOTAP) and dioleoylphosphatidylethanolamine (DOPE) and/or cholesterol (chol); and a mixture of dimethyldioctadecylammonium bromide (DDAB) and DOPE and/or chol. The ratio of the lipids can be varied to optimize the efficiency of uptake of the nucleic acid molecules for the specific target cell type. The liposome can comprise a mixture of one or more cationic lipids and one or more neutral or helper lipids. A desirable ratio of cationic lipid(s) to neutral or helper lipid(s) is about 1:(0.5-3), preferably about 1:(1-2) (molar ratio). Examples of ratios of various lipids useful in the practice of the present invention include, but are not limited to:

| | | |
|---|---|---|
| LipA | DOTAP/DOPE | 1:1 molar ratio |
| LipB | DDAB/DOPE | 1:1 molar ratio |
| LipC | DDAB/DOPE | 1:2 molar ratio |
| LipD | DOTAP/Chol | 1:1 molar ratio |
| LipE | DDAB/Chol | 1:1 molar ratio |

-continued

| | | |
|---|---|---|
| LipG | DOTAP/DOPE/Chol | 2:1:1 molar ratio |
| LipH | DDAB/DOPE/Chol | 2:1:1 molar ratio |

(DOTAP = dioleoyltrimethylaminnonium phosphate, DDAB = dimethyldioctadecylammonium bromide; DOPE = dioleoylphosphatidylethanolamine; chol = cholesterol).

As discussed throughout, in suitable embodiments, the ligand used in the compositions and methods of the present invention is an antibody fragment, for example a single chain Fv fragment, such as, an anti-transferrin receptor single chain Fv (TfRscFv). Suitably, the antibody or antibody fragment is mixed with the cationic liposome at a ratio in the range of about 1:1 to about 1:100, suitably about 1:10 to about 1:50 (w:w), more suitably about 1:30, or about 1:33 (antibody or antibody fragment:lipid) to form the targeted cationic liposome. In additional embodiments, the liposomes can also comprise endosomal disrupting peptides, such as the K[K(H)KKK]$_5$-K(H)KKC (HoKC) (HK) (SEQ ID NO: 1) peptide manufactured by Sigma-Genosys (The Woodlands, Tex.), associated with the liposomes. The endosomal disrupting peptide HoKC may help the release of agents in the cytoplasm of the cells.

In exemplary embodiments, cationic liposomal formulations A (DOTAP:DOPE at a 1:1 molar ratio), B (DDAB: DOPE at 1:1), G (DOTAP:DOPE:cholesterol at 1:1:1) and H (DDAB:DOPE:cholesterol at 1:1:1) or any of the lipid formulations described throughout, are prepared using the ethanol injection method as described herein and in the Examples. Only when a peptide (such as the K[K(H)KKK]$_5$-K(H)KKC (HoKC) (HK) peptide) is included in the complex, each liposome formulation also suitably includes MPB-DOPE at 5 molar percent of total lipid. Complexes prepared without the peptide do NOT contain MPB-DOPE and thus a ligand cannot be bound to the liposome via chemical conjugation.

Since the HoKC peptide (K[K(H)KKK]$_5$-K(H)KKC) (SEQ ID NO: 1) carries a terminal cysteine, MPB-DOPE was included in all of the liposome compositions to allow conjugation of peptide to the liposome. The Lip-HoKC liposomes were prepared using the coupling reaction between the cationic liposomes carrying the maleimide group (Lip-MPB) and the peptide. An aliquot of 0.1 mMol of the peptide with a free thiol group on cysteine was added to 2 mMol of Lip-MPB in 10 mM HEPES, pH 7.4, solution and rotated at room temperature (20-30 r.p.m.) for 2 h. The resulting Lip-HoKC has a lipid concentration of 1.4 mM.

The full complex is formed in a manner identical to that used to produce the TfRscFv:Lip:DNA complex without HoKC. Here also the anti-transferrin receptor single chain antibody fragment (TfRscFv) is mixed with Lip-HoKC by gentle inversion at a specific ratio, and incubated at room temperature for 10 min. Nucleic acid is then added to the TfRscFv:Lip-HoKC solution, mixed by gentle inversion and again incubated at room temperature for 15 min, after which dextrose or sucrose is added to a final concentration of 5-10% and again mixed by gentle inversion. A suitable ratio for the TfRscFv:Lip-HoKC:Nucleic acid complex is 0.3 mg:7 nmol:1 mg.

In additional embodiments, the methods of the present invention comprise preparing a ligand (e.g., protein/peptide, antibody or antibody fragment), and chemically conjugating the ligand to the surface of a cationic liposome to form a cationic immunoliposome. The cationic liposome is then mixed with a plasmid construct (vector) encoding BChE, and a plasmid construct (vector) encoding a polyproline rich peptide, to form the ligand-targeted liposome complex.

Exemplary methods, composition, ratios and conditions for chemically conjugating ligands (e.g., proteins/peptides, antibodies or antibody fragments) to cationic liposomes are disclosed in U.S. Pat. No. 7,479,276, the disclosure of which is incorporated by reference herein in its entirety.

As used herein the terms "protein" "peptide" and "polypeptide" are used interchangeably to mean any chain or chains of two or more amino acids, and does not refer to a specific length of product. Thus, peptides, dipeptides, tripeptides, oligopeptides, "protein," "amino acid chain," or any other term used to refer to a chain or chains of two or more amino acids, are included within the definition of the terms "protein," "polypeptide," and "peptide."

The present invention also provides cationic liposome complexes prepared according to the methods described throughout. For example, the present invention provides ligand-targeted (e.g., protein/peptide, antibody- or antibody fragment-targeted) cationic liposome complexes comprising a cationic liposome, a ligand (e.g., protein/peptide, antibody or antibody fragment), one or more nucleic acid molecules encoding BChE, and one or more nucleic acid molecules encoding a polyproline rich peptide, wherein the ligand is directly complexed/associated with, but not chemically conjugated to the cationic liposome. The ligand (e.g., protein/peptide, antibody or antibody fragment) is suitably associated with the liposome via an interaction (e.g., electrostatic, van der Walls, or other non-chemically conjugated interaction) between the ligand and the liposome. In general, a linker or spacer molecule (e.g., a polymer or other molecule) is not used to attach the ligands and the liposome when non-chemically conjugated.

As described herein, in additional embodiments, the ligand (e.g., protein/peptide, antibody or antibody fragment) is chemically conjugated to the cationic liposomes, for example, via a chemical interaction between the cationic liposome which contains a maleimidyl group or other sulfhydryl-reacting group, and a sulfur atom on the ligand (e.g., protein/peptide, antibody or antibody fragment). The nucleic acids are then added to the liposome to form the liposome-DNA complexes, or the nucleic acids can be added first, and then complexed with the ligands. Such methods are disclosed in U.S. Pat. No. 7,479,276, the disclosure of which is incorporated by reference herein in its entirety.

The nucleic acid molecules can be encapsulated within the cationic liposome, contained within a hydrocarbon chain region of the cationic liposome, associated with an inner or outer monolayer of the cationic liposome (e.g., the head-group region), or any combination thereof. Suitably, the cationic liposomes of the present invention are unilamellar liposomes (i.e. a single bilayer), though multilamellar liposomes which comprise several concentric bilayers can also be used. Single bilayer cationic liposomes of the present invention comprise an interior aqueous volume in which nucleic acid molecules can be encapsulated. They also comprise a single bilayer which has a hydrocarbon chain region (i.e. the lipid chain region of the lipids) in which nucleic acid molecules that have been conditioned to be neutral or largely uncharged can be contained. In addition, nucleic acid molecules can be complexed or associated with either, or both, the inner monolayer and/or the outer monolayer of the liposome membrane (i.e., the head-group region of the lipids), e.g., via a charge-charge interaction between the negatively charged nucleic acid molecules and the positively charged cationic liposomes. In further embodiments, nucleic acid molecules can be encapsulated/associated/complexed in any or all of these regions of the cationic liposome complexes of the present invention.

As discussed throughout, suitably the nucleic acid molecules are present at a molar ratio of about 0.1 mole of one or more nucleic acid molecules encoding butyrylcholinesterase (BChE), to about 10 mole of one or more nucleic acid molecules encoding a polyproline rich peptide; to 10 mole of one or more nucleic acid molecules encoding butyrylcholinesterase (BChE), to about 0.1 mole of one or more nucleic acid molecules encoding a polyproline rich peptide; in further embodiments the nucleic acid molecules are present at a molar ratio of about 1 mole of one or more nucleic acid molecules encoding butyrylcholinesterase (BChE), to about 10 mole of one or more nucleic acid molecules encoding a polyproline rich peptide; to 10 mole of one or more nucleic acid molecules encoding butyrylcholinesterase (BChE), to about 1 mole of one or more nucleic acid molecules encoding a polyproline rich peptidemore suitably the nucleic acid molecules are present at a molar ratio of about 5 mole of one or more nucleic acid molecules encoding butyrylcholinesterase (BChE), to about 1 mole of one or more nucleic acid molecules encoding a polyproline rich peptide; to 1 mole of one or more nucleic acid molecules encoding butyrylcholinesterase (BChE), to about 5 mole of one or more nucleic acid molecules encoding a polyproline rich peptide; in particular, about 4 mole of one or more nucleic acid molecules encoding butyrylcholinesterase (BChE), to about 1 mole of one or more nucleic acid molecules encoding a polyproline rich peptide, in particular, about 2 mole of one or more nucleic acid molecules encoding butyrylcholinesterase (BChE), to about 1 mole of one or more nucleic acid molecules encoding a polyproline rich peptide, in particular, about 1 mole of one or more nucleic acid molecules encoding butyrylcholinesterase (BChE), to about 1 mole of one or more nucleic acid molecules encoding a polyproline rich peptide can be used in the liposome complexes. Suitable amounts/ratios of lipids, targeting ligands and nucleic acid molecules are also described throughout.

In exemplary embodiments, the one or more nucleic acid molecules encoding butyrylcholinesterase (BChE), the one or more nucleic acid molecules encoding a polyproline rich peptide, and the liposomes, are present at a weight ratio of between about 0.5:1 to about 1:40 (μg total nucleic acid:μg lipid), suitably about 1:1 to about 1:40 (μg total nucleic acid:μg lipid), or about 1:5 to about 1:20 (μg total nucleic acid:μg lipid), e.g., about 1:10 (μg total nucleic acid:μg lipid). An exemplary liposome composition of the present invention comprises total nucleic acid, lipid and a ligand, such as a single chain antibody (e.g., TfscFv) at a weight ratio of about 1:10:0.33 (μg total nucleic acid:μg lipid:μg single chain antibody) (also referred to herein as scL).

The present invention also provides pharmaceutical compositions comprising the ligand-targeted cationic liposome complexes described throughout. In suitable embodiments, the pharmaceutical compositions further comprise one or more excipients selected from the group consisting of one or more antibacterials (e.g., amphotericin B, chloretracycline, gentamicin, neomycin), one or more preservatives (e.g., benzethonium chloride, EDTA, formaldehyde, 2-phenoxyethanol), one or more buffers (e.g., phosphate buffers, sodium borate, sodium chloride), one or more surfactants (polysorbate 20, 80), one or more protein stabilizers (e.g., albumin, lactose, potassium glutamate), sugars e.g. sucrose or dextrose, and adjuvants (e.g., aluminum hydroxide, aluminum phosphate). Additional excipients are well known in the art and can be readily used in the practice of the present invention.

In certain such embodiments, the nucleic acid molecules encoding butyrylcholinesterase (BChE) are delivered in the same composition as the nucleic acids encoding a polyproline rich peptide, but rather than being encapsulated/associated with the same cationic liposome, they are associated with two (or more) different cationic liposomes and then delivered in the same composition (i.e., two different liposome populations mixed together). In other embodiments the nucleic acid molecules encoding BChE and the nucleic acid molecules encoding a polyproline rich peptide can be contained together within the same plasmid vector. The present invention also encompasses administering to a mammal two separate liposome compositions, one which comprises nucleic acids encoding BChE, and one which comprises nucleic acids encoding a polyproline rich peptide. Examples of suitable lipids, targeting molecules and nucleic acid molecules, and ratios of such components for use the pharmaceutical compositions of the present invention are described throughout.

Methods of Treatment and/or Prevention

Also provided herein are methods of treating and/or preventing toxicity associated with exposure to an organophosphate agent in a mammal. Suitably such methods comprise administering to the mammal a cationic liposome complex, wherein the cationic liposome complex comprises a cationic liposome, a ligand directly complexed with, but not chemically conjugated to, the cationic liposome, a nucleic acid molecule (including one or more than one nucleic acid molecules) encoding butyrylcholinesterase (BChE) associated with the cationic liposome, and a nucleic acid molecule (including one or more than one nucleic acid molecules) encoding a polyproline rich peptide associated with the same or a different cationic liposome.

The methods described herein can be utilized with any mammal, including humans, dogs, cats, mice, rats, monkeys, etc.

Suitably, the methods are for the treatment of toxicity associated with exposure to the organophosphate agent. As used herein, methods "for treatment" of the toxicity associated with exposure to an OP agent provide a therapeutically effective amount of BChE and a polyproline rich peptide so as to allow the mammal to overcome the toxicity associated with exposure to an OP agent, after the mammal has been exposed to the OP agent.

In further embodiments, the methods are for the prevention of toxicity associated with exposure to the organophosphate agent. As used herein, methods "for prevention" of the toxicity associated with exposure to an OP agent provide a therapeutically effective amount of BChE and a polyproline rich peptide before (i.e., if) the mammal is exposed to the OP agent, so as to allow the mammal to overcome the toxicity associated with a future exposure to an OP agent.

The phrase "therapeutically effective amount" is used here to mean an amount sufficient to reduce by at least about 10 percent, suitably at by at least 20 percent, or by at least 30 percent, or by at least 40 percent, more suitably by at least 50-90 percent, and still more suitably prevent (i.e. reduce by 100 percent), a clinically significant deficit in the activity, function and response of the mammal to the toxicity associated with the OP agent. In addition, a "therapeutically effective amount" is suitably also sufficient to cause an improvement in a clinically significant condition in the mammal.

In the context of detoxifying agents (i.e., BChE), often the level of effectiveness is defined in terms of protecting/scavenging/detoxifying a certain amount of toxic agent (OP). A useful metric is "$LD_{50}$," which is the amount of chemical that is lethal to one half of the animals exposed to the chemical agent. Thus, a "therapeutically effective amount" is also an amount that is sufficient to protect against at least one $LD_{50}$ (i.e., $1 \times LD_{50}$—1 times $LD_{50}$) of the toxic agent (OP). As described herein, the methods provided suitably deliver amounts of detoxifying agent that can treat the effects of exposure to, or prevent the potential exposure to, at least 1, at least 2, at least 3, at least 4, at least 5, at least 6 times (or more) the $LD_{50}$ of the OP agent.

Suitably the complex is administered so as to treat toxicity associated with exposure to at least $1 \times LD_{50}$ of the organophosphate agent, up to and including, $5 \times LD_{50}$ of the organophosphate agent.

In other embodiments, the complex is administered so as to prevent toxicity associated with the potential exposure to at least $1 \times LD_{50}$ of the organophosphate agent, up to and including $5 \times LD_{50}$ of the organophosphate agent.

Any suitable method can be used to administer the complexes as described herein to the mammal. In embodiments, the complex is administered via a route selected from the group consisting of intranasal administration, intravenous administration, oral administration, sublingual administration, intramuscular administration, intralesional administration, intradermal administration, transdermal administration, intraocular administration, intraperitoneal administration, percutaneous administration, aerosol administration, intraorgan administration, intracerebereal administration, topical administration, subcutaneous administration, endoscopic administration, slow release implant, administration via an osmotic or mechanical pump and administration via inhalation. Most suitably, the complex is administered via intranasal or aerosol inhalation administration, resulting in pulmonary delivery of the complexes and nucleic acids.

Pulmonary delivery devices for administration of the complexes described herein are well known in the art. Pulmonary delivery devices generate particles of active agent, typically about 0.01 μm to about 4 μm, which may be inhaled by the subject. Pulmonary delivery devices are widely used for inhalation of an active agent (i.e., the liposome complexes described herein) from solution or suspension, or inhalation of an active agent in dry powder form, optionally admixed with an excipient. Examples of pulmonary delivery devices include, but are not limited to, metered dose inhalers (MDIs), nebulizers, and dry powder inhalers (DPIs). The pulmonary delivery devices may optionally be pressurized, and may utilize propellant systems. The pulmonary delivery devices may also incorporate holding chambers, e.g., spacers, to prevent aerosolized active agents from escaping into the air, and allowing the subject more time to inhale.

Pulmonary delivery devices utilized in the methods described herein may be activatable by inhalation, e.g., will automatically dispense active agent upon inhalation by the subject, and may be used with aerosol containers which contain active agents and optionally contain propellants. These devices can administer a plurality of metered doses in a controlled manner, allowing controlled and consistent dosing of active agents into the subject's bronchial passages and pulmonary epithelium. Examples of pulmonary delivery devices are described in U.S. Pat. Nos. 5,290,539, 6,615,826, 4,349,945, 6,460,537, 6,029,661, 5,672,581, 5,586,550, and 5,511,540, which are incorporated by reference herein.

Metered Dose Inhalers (MDIs) operate by utilizing a propellant to eject a constant volume of an active agent, which is inhaled by the subject. MDIs may also include a surfactant to prevent aggregation of the active agent. The active agent may be dissolved or suspended in solution. MDIs utilizing propellants may require simultaneous inhalation and activation of the MDI. Holding chambers, e.g., spacers, may be used to store the aerosolized active agent, eliminating the need for simultaneous activation and inhalation. MDIs provide a constant, metered dosage of the active agent and allow for consistent dosing. Examples of MDIs are described in U.S. Pat. Nos. 6,615,826 and 5,290,539.

Nebulizers operate by creating a mist, i.e., nebulizing or atomizing, a formulation of active agent in solution, which is inhaled by the subject. The active agent may be dissolved or suspended in solution. The droplets may be created by any method known in the art, including the use of a fan, a vibrating member, or ultrasonic apparatus. Nebulizers are more gentle than MDIs and DPIs, and are appropriate for individuals unable to use inhalers, such as infants, young children, and individuals that are seriously ill or incapacitated. Examples of nebulizers are described in U.S. Pat. Nos. 6,748,945, 6,530,370, 6,598,602, and 6,009,869.

Dry Powder Inhalers (DPIs) do not use propellants, and administer dry powder which is inhaled by the subject. To distribute the dry powder, DPIs may utilize any method known in the art to propel the active agent, including pneumatic systems, powered fans, or mechanical propulsion, e.g., squeezing of the container. DPIs may instead rely simply upon the inhalation by the subject. Blending of active agent with propellants is not required for DPIs, allowing delivery of larger payloads of active agent. An example of a DPI is described in U.S. Pat. No. 6,029,661.

Often, the aerosolization of a liquid or a dry powder formulation for inhalation into the lung will require a propellant. The propellant may be any propellant generally used in the art. Specific non-limiting examples of such useful propellants are a chlorotlourocarbon, a hydrofluorocarbon, a hydochlorofluorocarbon, or a hydrocarbon, including triflouromethane, dichlorodiflouromethane, dichlorotetrafiioroethanol, and 1,1,1,2-tetraflouroethane, or combinations thereof. Examples of propellant formulations are described in U.S. Pat. No. 5,672,581, which is incorporated herein by reference.

Other methods known in the art for pulmonary administration can also be used. By way of example, these methods include delivery by intratracheal inhalation, insufflation, or intubation, e.g., the delivery of a solution, a powder, or a mist into the lungs by a syringe, tube, or similar device.

As described herein, suitably the ligand for use in the complexes is transferrin, an antibody and an antibody fragment. Exemplary antibodies and antibody fragments are described throughout and include single chain Fv antibody fragment, such as an anti-transferrin receptor single chain Fv (TfRscFv).

In embodiments, the ligand-targeted cationic liposomes further comprise a peptide comprising a K[K(H)KKK]5-K(H)KKC (HoKC) (SEQ ID NO: 1) peptide associated with the cationic liposome. Exemplary methods of associating the peptide with the cationic liposomes are described herein.

In suitable embodiments, the nucleic acid molecule encoding BChE is contained in a first plasmid and the nucleic acid molecule encoding the polyproline rich peptide is contained in a second plasmid. That is, the nucleic acid molecules are contained in separate plasmids, each of which plasmids are associated (i.e., encapsulated) with the same or different cationic liposomes. In further embodiments, the nucleic acid molecule encoding BChE and the nucleic acid molecule encoding the polyproline rich peptide can be contained in the same plasmid, i.e., expressed from the same plasmid. However, by utilizing two separate plasmids, the amount of each nucleic acid, and thus the amount of each expressed protein, can be controlled separately and the ratios of the nucleic acids optimized for various treatment or prevention protocols and effects.

Suitably, the nucleic acid molecule encoding BChE is contained in a first plasmid construct, comprising, from 5' to 3': (a) at least one human adenovirus enhancer sequence; (b) a cytomegalovirus (CMV) promoter; (c) a multiple cloning site; (d) the nucleic acid molecule encoding BChE; and (e) an SV 40 poly A sequence, wherein the 3' end of the plasmid construct does not comprise adenovirus map units 9-16 when compared to a wild-type adenovirus. In embodiments, the nucleic acid molecule encoding the polyproline rich peptide is contained in a second plasmid construct, comprising, from 5' to 3': (a) at least one human adenovirus enhancer sequence; (b) a cytomegalovirus (CMV) promoter; (c) a multiple cloning site; (d) the nucleic acid molecule encoding the polyproline rich peptide; and (e) an SV 40 poly A sequence, wherein the 3' end of the plasmid construct does not comprise adenovirus map units 9-16 when compared to a wild-type adenovirus. See FIG. 3 of U.S. Published Patent Application No. 2007/0065432, which is specifically incorporated by reference herein, which describes such constructs. In further embodiments, the nucleic acids can be expressed by other promoters known in the art.

In exemplary embodiments, the BChE that is expressed by the nucleic acids is a mutant version of BChE. Suitable mutants of BChE are known in the art or otherwise described herein, and suitably include the G117H mutant, as described in Millard, C. B., Lockridge, O., & Broomfield, C. A. (1995), "Design and expression of organophosphorus acid anhydride hydrolase activity in human butyrylcholinesterase," *Biochemistry* 34: 15925-15933; and Lockridge, O., Blong, R. M., Masson, P., Froment, M. T., Millard, C. B., & Broomfield, C. A. (1997), "A single amino acid substitution, Gly117His, confers phosphotriesterase (organophosphorus acid anhydride hydrolase) activity on human butyrylcholinesterase," Biochemistry 36:786-795, the disclosures of each of which are incorporated by reference herein in their entireties.

As described herein, suitably the cationic liposome comprises a mixture of one or more cationic lipids and one or more neutral or helper lipids. Exemplary ratios of ligand: cationic liposome are described throughout, and suitably include where the ligand and the cationic liposome are present at a ratio in the range of about 1:1 to about 1:100 (w:w), suitably where the ligand and the cationic liposome are present at a ratio in the range of about 1:10 to about 1:50 (w:w), or more suitably where the ligand and the cationic liposome are present at a ratio in the range of about 1:20 to about 1:40 (w:w).

In embodiments, the cationic liposomes for use in the methods described herein comprise a mixture of dioleoyltrimethylammonium phosphate with dioleoylphosphatidylethanolamine and cholesterol; a mixture of dioleoyltrimethylammonium phosphate with cholesterol, a mixture of dimethyldioctadecylammonium bromide with dioleoylphosphatidylethanolamine and cholesterol, a mixture of dimethyldioctadecylammonium bromide with dioleoylphosphatidylethanolamine, a mixture of dimethyldioctadecylammonium bromide with cholesterol, or a mixture of dioleoyltrimethylammonium phosphate with dioleoylphosphatidylethanolamine. Additional liposome compositions that can be utilized in the methods are described herein.

In suitable embodiments, the nucleic acid molecules are present at a molar ratio of about 10:1 to about 1:10 (moles nucleic acid molecule encoding butyrylcholinesterase (BChE): moles nucleic acid molecule encoding a polyproline rich peptide). More suitably, the nucleic acid molecules are present at a molar ratio of about 8:1 to about 1:8 (moles nucleic acid molecule encoding butyrylcholinesterase (BChE):moles nucleic acid molecule encoding a polyproline rich peptide), or a molar ratio of about 7:1 to about 1:7 (moles nucleic acid molecule encoding butyrylcholinesterase (BChE):moles nucleic acid molecule encoding a polyproline rich peptide), a molar ratio of about 6:1 to about 1:6 (moles nucleic acid molecule encoding butyrylcholinesterase (BChE):moles nucleic acid molecule encoding a polyproline rich peptide) a molar ratio of about 5:1 to about 1:5 (moles nucleic acid molecule encoding butyrylcholinesterase (BChE):moles nucleic acid molecule encoding a polyproline rich peptide), a molar ratio of about 4:1 to about 1:4 (moles nucleic acid molecule encoding butyrylcholinesterase (BChE):moles nucleic acid molecule encoding a polyproline rich peptide), a molar ratio of about 3:1 to about 1:3 (moles nucleic acid molecule encoding butyrylcholinesterase (BChE):moles nucleic acid molecule encoding a polyproline rich peptide), a molar ratio of about 2:1 to about 1:2 (moles nucleic acid molecule encoding butyrylcholinesterase (BChE):moles nucleic acid molecule encoding a polyproline rich peptide), or a molar ratio of about 1:1 (moles nucleic acid molecule encoding butyrylcholinesterase (BChE):moles nucleic acid molecule encoding a polyproline rich peptide).

Suitable ratios for the total amount of nucleic acid (i.e. the amount nucleic acid molecules encoding butyrylcholinesterase (BChE) combined with the nucleic acid molecules encoding a polyproline rich peptide) to the amount of liposome are described herein. In suitable embodiments, the weight ratio is between about 1:1 to about 1:40 (μg nucleic acid:μg liposome), more suitably the weight ratio is between about 1:5 to about 1:20 (μg total nucleic acid:μg liposome), or the weight ratio is about 1:10 (μg total nucleic acid:μg liposome).

Suitably, the nucleic acid molecules are encapsulated within the interior of the cationic liposome, though in other embodiments the nucleic acid molecules can be associated with an inner or outer monolayer of the cationic liposome (e.g., the head-group region).

In suitable embodiments of the methods of treating toxicity associated with exposure to an OP agent, the complexes described herein are administered immediately after exposure to the organophosphate agent, i.e., within seconds (10, 20, 30, seconds, etc.) minutes (1, 5, 10, 15, 20, or 30 or more minutes), hours (i.e., 1, 2, 3, 4, 5 or more hours) or days (i.e., 1, 2, 3, 4, 5 or more days) after the mammal is contacted with the OP agent. In general, such contact with the OP agent will be via inhalation of the agent and/or contact with the skin, eyes or mucus membranes of the mammal.

In suitable embodiments of the methods of preventing toxicity associated with exposure to an OP agent, the complexes described herein are administered at least 6 hours prior to a potential exposure to the organophosphate agent. Suitably, the complexes described herein are administered at least 10 hours, at least 12 hours, at least 15 hours, at least 20 hours, at least 24 hours, at least 36 hours or at least 48 hours prior to the potential exposure to the organophosphate agent. In additional embodiments the complexes are administered at least 2 days, at least 3 days, at least 4 days, at least 5 days, at least 6 days, at least 7 days, at least 8 days, at least 9 days, at least 10 days, at least 11 days, at least 12 days, at least 13 days or at least 14 days prior to the potential exposure to the organophosphate agent. Suitably, the complex is administered at least once a week, more suitably at least twice a week, etc., prior to potential exposure to the OP agent. In further embodiments, the administration can be once every 10-14 days, prior to potential exposure to the OP agent.

In further embodiments, methods of treating toxicity associated with exposure to an organophosphate agent in a human are provided. Such methods suitably comprise administering intranasally or via aerosol inhalation to the human a cationic liposome complex as described herein. Suitably the cationic liposome complex comprises a cationic liposome, an anti-transferrin receptor single chain Fv (TfRscFv) directly complexed with, but not chemically conjugated to, the cationic liposome, a nucleic acid molecule encoding butyrylcholinesterase (BChE) contained in a first plasmid associated with the cationic liposome, and a nucleic acid molecule encoding a polyproline rich peptide contained in a second plasmid associated with the cationic liposome. Suitably the TfRscFv and the cationic liposome are present at a ratio in the range of about 1:20 to about 1:40 (w:w) and the nucleic molecules are present at a ratio of about 1:5 to about 1:20 (μg nucleic acid:μg liposome). In embodiments the complex is administered so as to treat toxicity associated with exposure of at least $1 \times LD_{50}$ of the organophosphate agent.

Also provided are methods of preventing toxicity associated with exposure to an organophosphate agent in a human. Such methods suitably comprise administering intranasally or via aerosol inhalation to the human a cationic liposome complex. Suitably the cationic liposome complex comprises a cationic liposome, an anti-transferrin receptor single chain Fv (TfRscFv) directly complexed with, but not chemically conjugated to, the cationic liposome, a nucleic acid molecule encoding butyrylcholinesterase (BChE) contained in a first plasmid associated with the cationic liposome, and a nucleic acid molecule encoding a polyproline rich peptide contained in a second plasmid associated with the cationic liposome. Suitably the TfRscFv and the cationic liposome are present at a ratio in the range of about 1:20 to about 1:40 (w:w) and the nucleic molecules are present at a ratio of about 1:5 to about 1:20 (μg total nucleic acid:μg liposome). Suitably the complex is administered so as to prevent toxicity associated with exposure of at least $1 \times LD_{50}$ of the organophosphate agent.

As described throughout, suitably the nucleic acid molecule encoding BChE is contained in a first plasmid construct, comprising, from 5' to 3': (a) at least one human adenovirus enhancer sequence; (b) a cytomegalovirus (CMV) promoter; (c) a multiple cloning site; (d) the nucleic acid molecule encoding BChE; and (e) an SV 40 poly A sequence, wherein the 3' end of the plasmid construct does not comprise adenovirus map units 9-16 when compared to a wild-type adenovirus. In embodiments the nucleic acid molecule encoding the polyproline rich peptide is contained in a first plasmid construct, comprising, from 5' to 3': (a) at least one human adenovirus enhancer sequence; (b) a cytomegalovirus (CMV) promoter; (c) a multiple cloning site; (d) the nucleic acid molecule encoding the polyproline rich peptide; and (e) an SV 40 poly A sequence, wherein the 3' end of the plasmid construct does not comprise adenovirus map units 9-16 when compared to a wild-type adenovirus.

In embodiments, BChE is a mutant version of BChE, such as a G117H mutant.

Exemplary lipids, ratios of nucleic acids to liposomes and exemplary ratios of the nucleic acids associated with the liposomes are described herein.

Suitably the nucleic acid molecules are present at a molar ratio of about 10:1 to about 1:10 (moles nucleic acid molecule encoding butyrylcholinesterase (BChE):moles nucleic acid molecule encoding a polyproline rich peptide), more suitably the nucleic acid molecules are present at a molar ratio of about 5:1 to about 1:5 (moles nucleic acid molecule encoding butyrylcholinesterase (BChE):moles nucleic acid molecule encoding a polyproline rich peptide), most suitably the nucleic acid molecules are present at a molar ratio of about 4:1 (moles nucleic acid molecule encoding butyrylcholinesterase (BChE):moles nucleic acid molecule encoding a polyproline rich peptide) or about 2 mole of one or more nucleic acid molecules encoding butyrylcholinesterase (BChE), to about 1 mole of one or more nucleic acid molecules encoding a polyproline rich peptide, or about 1 mole of one or more nucleic acid molecules encoding butyrylcholinesterase (BChE), to about 1 mole of one or more nucleic acid molecules encoding a polyproline rich peptide.

Suitably the nucleic acid molecules are encapsulated within the interior of the cationic liposome.

As described herein, suitable the complex is administered so as to treat toxicity associated with exposure of up to $5 \times LD_{50}$ of the organophosphate agent. In embodiments, the complex is administered immediately after exposure to the organophosphate agent.

As described herein, suitably the complex is administered so as to prevent toxicity associated with exposure of up to $5 \times LD_{50}$ of the organophosphate agent. Suitably the complex is administered at least 6 hours prior to potential exposure to the organophosphate agent. In embodiments, the complex is administered at least once a week prior to potential exposure to the organophosphate agent.

Also provided herein are methods of delivering butyrylcholinesterase (BChE) to the bloodstream of a mammal (e.g., a human) comprising administering intranasally or via aerosol inhalation to the mammal a cationic liposome complex. As described herein, suitably the cationic liposome complex comprises a cationic liposome, an anti-transferrin receptor single chain Fv (TfRscFv) directly complexed with, but not chemically conjugated to, the cationic liposome, a nucleic acid molecule encoding butyrylcholinesterase (BChE) contained in a first plasmid associated with the cationic liposome, and a nucleic acid molecule encoding a polyproline rich peptide contained in a second plasmid associated with the same or different cationic liposome.

Suitably the TfRscFv and the cationic liposome are present at a ratio in the range of about 1:20 to about 1:40 (w:w) and the nucleic molecules are present at a ratio of about 1:5 to about 1:20 (μg nucleic acid:μg liposome).

In embodiments of the various methods described herein, suitably the complex is administered so as to result in an amount of BChE in the bloodstream of the human of at least 250 mg/70 kg (weight of BChE/weight of the human). Suitably, the complex is administered so as to result in an amount of BChE in the bloodstream of the human of at least 200 mg/70 kg (weight of BChE/weight of the human), more suitably at least 225 mg/70 kg, at least 250 mg/70 kg, at least 275 mg/70 kg, at least 300 mg/70 kg, at least 325 mg/70 kg at least 350 mg/70 kg, or at least 400 mg/70 kg.

As described throughout, suitably the nucleic acid molecule encoding BChE is contained in a first plasmid construct, comprising, from 5' to 3': (a) at least one human adenovirus enhancer sequence; (b) a cytomegalovirus (CMV) promoter; (c) a multiple cloning site; (d) the nucleic acid molecule encoding BChE; and (e) an SV 40 poly A sequence, wherein the 3' end of the plasmid construct does not comprise adenovirus map units 9-16 when compared to a wild-type adenovirus. Suitably the nucleic acid molecule encoding the polyproline rich peptide is contained in a first plasmid construct, comprising, from 5' to 3': (a) at least one human adenovirus enhancer sequence; (b) a cytomegalovirus (CMV) promoter; (c) a multiple cloning site; (d) the nucleic acid molecule encoding the polyproline rich peptide; and (e) an SV 40 poly A sequence, wherein the 3' end of the plasmid construct does not comprise adenovirus map units 9-16 when compared to a wild-type adenovirus.

Alternatively the nucleic acid molecule encoding BChE, and the nucleic acid molecule encoding the polyproline rich peptide, are in the same construct, but the nucleic acid molecule encoding BChE is placed downstream from the high expression promoter disclosed in U.S. Published Patent Application No. 2007/0065432, while the nucleic acid molecule encoding the polyproline rich peptide is placed downstream of a standard promoter such as RSV or CMV In embodiments, the BChE is a mutant version of BChE, such as a G117H mutant.

Exemplary compositions of the liposomes and ratios for the various components are described herein. Suitably, the nucleic acid molecules are present at a molar ratio of about 10:1 to about 1:10 (moles nucleic acid molecule encoding butyrylcholinesterase (BChE):moles nucleic acid molecule encoding a polyproline rich peptide).

Suitably the nucleic acid molecules are present at a molar ratio of about 10:1 to about 1:10 (moles nucleic acid molecule encoding butyrylcholinesterase (BChE):moles nucleic acid molecule encoding a polyproline rich peptide), more suitably the nucleic acid molecules are present at a molar ratio of about 5:1 to about 1:5 (moles nucleic acid molecule encoding butyrylcholinesterase (BChE):moles nucleic acid molecule encoding a polyproline rich peptide), most suitably the nucleic acid molecules are present at a molar ratio of about 4:1 (moles nucleic acid molecule encoding butyrylcholinesterase (BChE):moles nucleic acid molecule encoding a polyproline rich peptide) or about 2 mole of one or more nucleic acid molecules encoding butyrylcholinesterase (BChE), to about 1 mole of one or more nucleic acid molecules encoding a polyproline rich peptide, or about 1 mole of one or more nucleic acid molecules encoding butyrylcholinesterase (BChE), to about 1 mole of one or more nucleic acid molecules encoding a polyproline rich peptide.

Suitably the liposome complexes described herein comprise two co-encapsulated plasmid vectors carrying the BChE genes (e.g., mutant BChE) and polyproline rich peptide genes, produce a level of tetrametic BChE (at least 40%, more preferably 70%-90% tetramer form) that is active in circulation for 1 to 21 days. The methods described herein suitably produce enzyme levels that obtain a therapeutically effective amount. It is unexpected that the complex of this invention encapsulating a plasmid vector encoding for BChE and a plasmid vector encoding for a polyproline rich peptide under the control of a high expression promoter can achieve the level of activity, and length of protein expression of active BChE.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Presence of Transgene (Exogenous p53) in Metastatic Tumors from Subjects in a Phase I Clinical Trial of scL Delivered Wtp53 Gene This example demonstrates a successful transgene delivered by the scL nanocomplex (a liposome composition of the present invention comprising total nucleic acid, lipid and the single chain antibody TfscFv at a weight ratio of about 1:10:0.33 (µg total nucleic acid:µg lipid:µg single chain antibody) (also referred to herein as scL), encoding exogenous wtp53 DNA, SGT-53, is present in the tumors of treated patients. To assess tumor delivery of SGT-53, DNA PCR was performed to determine the exogenous p53 gene delivered by the SGT-53 complex in the tumors from subjects in an open label, single center, sequential dose escalating, Phase 1 study evaluating the safety, pharmacokinetics, and potential activity of SGT-53 in subjects with solid tumors and who had been offered all standard or approved therapies. The doses of SGT-53 administered to the subjects escalated from 0.6 mg DNA/infusion to 3.6 mg DNA/infusion. Study drug was administered twice weekly for five weeks for a total of ten infusions. In 2 subjects a biopsy of the most accessible tumor was performed within 24 to 96 hours after the last administration of SGT-53. At least 20 mg of tumor tissue was obtained. A microscopic examination was performed on the frozen sample to ensure that the sample contained tumor. The tumor tissue was snap frozen and was used for DNA PCR to identify the presence and level of exogenous wtp53 DNA in the tumor. In both cases, the tumor sample was obtained from a metastatic lesion. A 700 bp fragment was amplified using one primer in the vector and one primer in the p53 insert. Using this approach, only the exogenous p53 transgene was amplified. Tumor biopsies were obtained from patients after the end of treatment with the lowest dose (0.6 mg/infusion) (T1) and with the 3.6 mg/infusion dose (T2). As shown in FIG. 1, the amplified 700 bp fragment of the exogenous p53 gene was clearly present in both tumors. More importantly, the transgene was present in a dose dependent manner as would be expected with targeted delivery.

EXAMPLE 2

Increase in Protein Expression after Cloning into the pSCMV Vector

Figure 2:
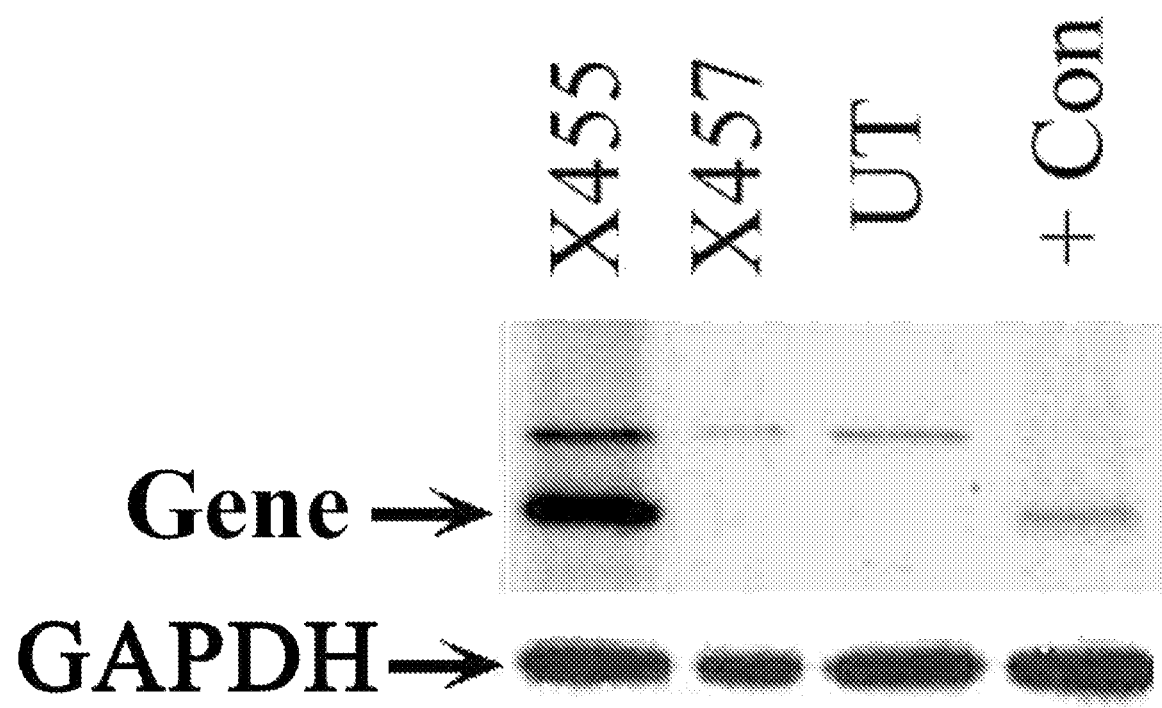
FIG. 2 shows increase in protein expression as a result of placing a gene under the control a high expression promoter as described herein.

The increase in protein expression as a result of placing a gene under the control a high expression promoter, as disclosed herein, is shown in FIG. 2. Human cells were transfected with scL (prepared as described below in Example 7) carrying a gene cloned into the pSCMV vector, or in the original construct. Twenty-four hours post-transfection, expression of the specific gene was assessed by Western analysis. The purified protein expressed from this specific gene is included on the gel as a positive control and for verification of protein positioning. An at least 10 fold higher level of the specific protein expression was observed with the pSCMV clone (X455) compared to that of the original construct (X457) which uses a standard promoter (FIG. 2). The specific band is present in X457 upon longer exposure (data not shown). GAPDH levels demonstrate equal protein loading. UT=untreated cells; +Con=purified protein to confirm position.

EXAMPLE 3

Figure 3A:
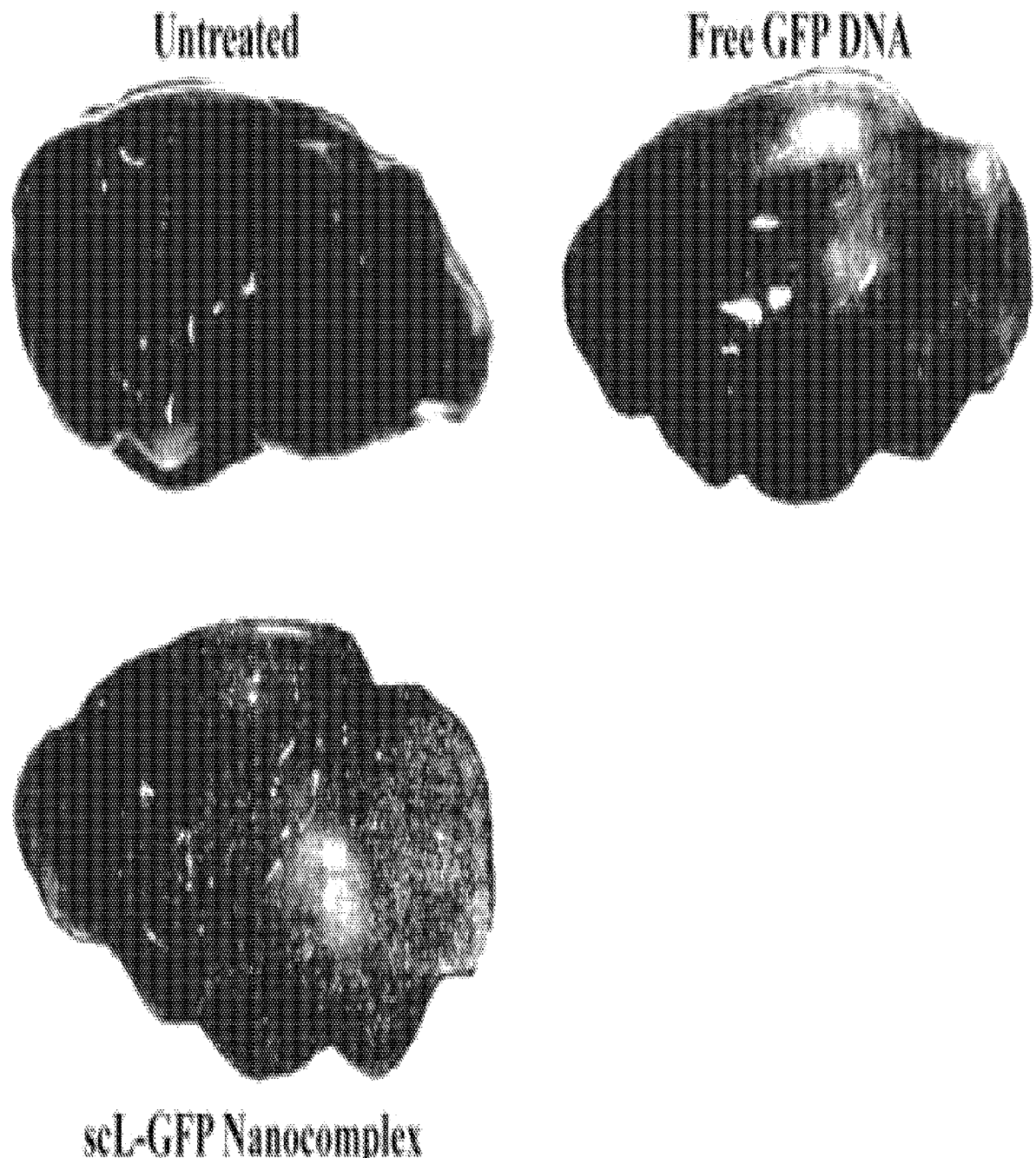
FIGS. 3A and 3B show scL delivery to the brain in Balb/C mice injected with scL carrying either the pSCMV high expression plasmid containing the GFP gene (FIG. 3A) or carrying a fluorescently labeled oligonucleotide (FIG. 3B).
Figure 3B:
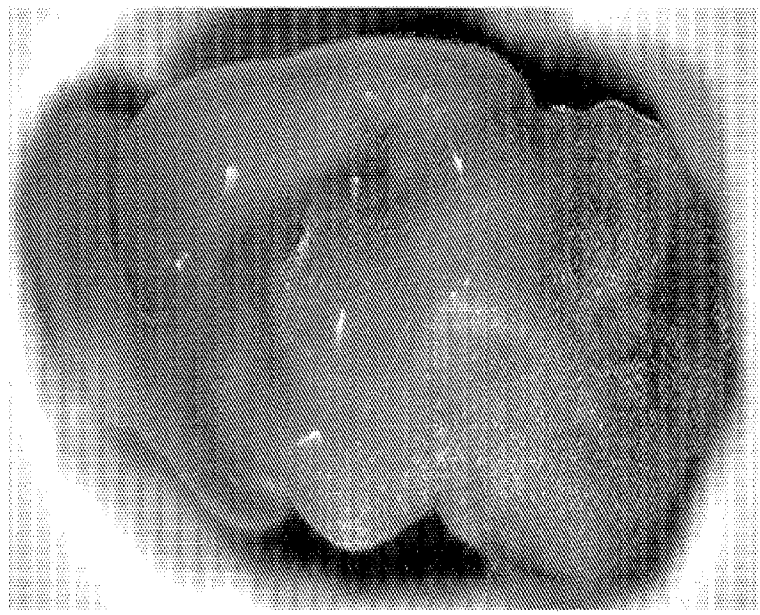
Figure 3B:
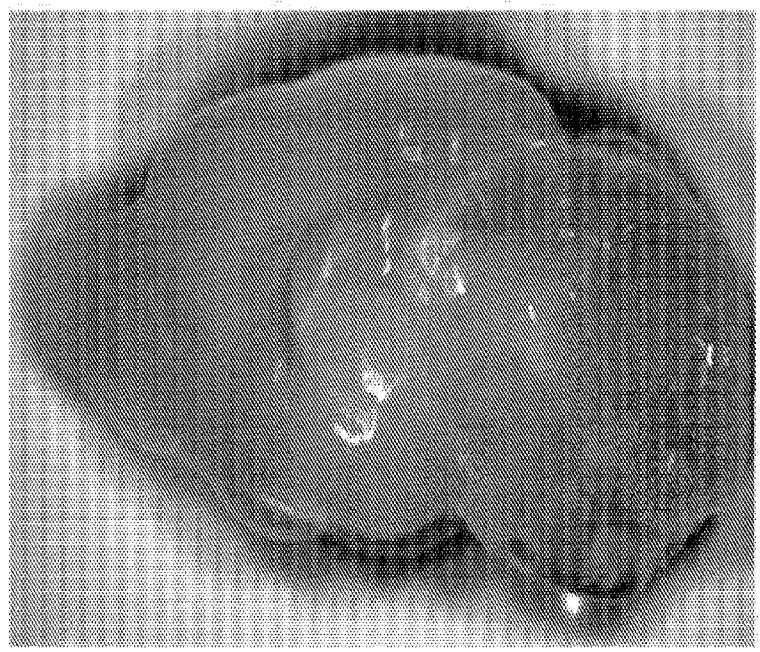
Figure 4A:
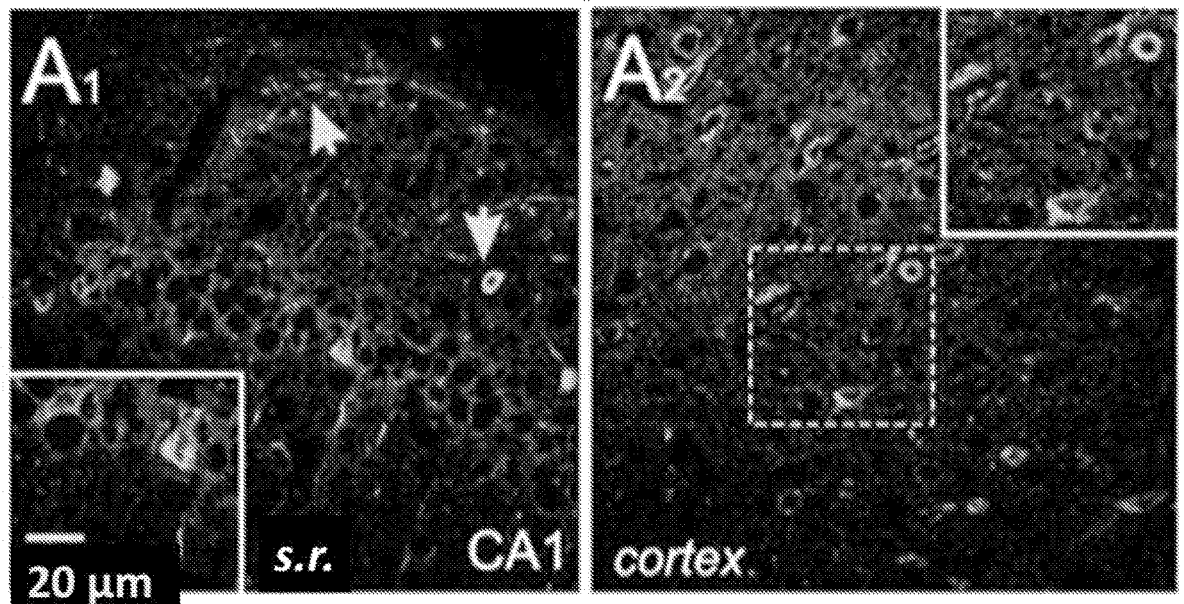
FIG. 4A-4B show brain sections of the liposome complex targeting the TfR and carrying a plasmid encoding GFP (100 µg cDNA) injected via a catheterized jugular vein in rats.
Figure 4B:
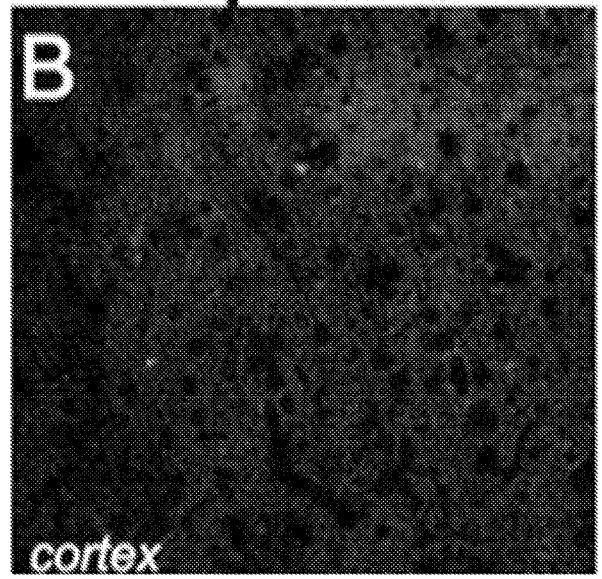

Ability of the scL Liposome Complex to Cross the Blood-Brain Barrier and Target Neuronal Cells The ability to cross the blood-brain barrier and target neuronal cells in the brain is shown in FIGS. 3 and 4. In FIG. 3, Balb/C mice were injected with scL carrying either the pSCMV high expression plasmid containing the GFP gene (FIG. 3A) or carrying a fluorescently labeled oligonucleotide (6-FAM-ODN) (FIG. 3B) prepared as described below in Example 7. 24 or 48 hours later the brains were excised and imaged using the Maestro® In Vivo Imaging System (Perkin Elmer). In both cases, a significantly higher level of accumulation of the fluorescence signal is observed in the brains of the mice injected with the scL-delivered payload when compared to the level of accumulation/signal with either Free (unencapsulated) GFP DNA or Free (unencapsulated) 6-FAM-ODN.

The ligand-liposome complex targeting the TfR and carrying a plasmid encoding GFP (100 µg cDNA) prepared as described below in Example 7 was injected via a catheterized jugular vein in rats. After 24-36 hours of post-surgery recovery, animals were sacrificed and coronal 40 µm brain sections analyzed via fluorescence microscopy. As expected, non-targeted liposome-GFP produced no detectable EGFP (+) cells in the brain (FIG. 4 B). In contrast, Tf-Lip-DNA injections yielded widespread EGFP expression (mainly in neuronal cells) in cortex and hippocampus, which indicate that TfR-targeted vectors cross the blood-brain barrier to deliver the genetic payload to adult neurons in vivo. Numerous EGFP(+) neurons (arrow) and neuropil (arrow) are observed in hippocampus (CA1 area) (A1) and cortex (A2) following iv injection of Tf-Lip-EGFP cDNA. Parvalbumin IF staining revealed innervation of EGFP(+) neurons.

EXAMPLE 4

Figure 5:
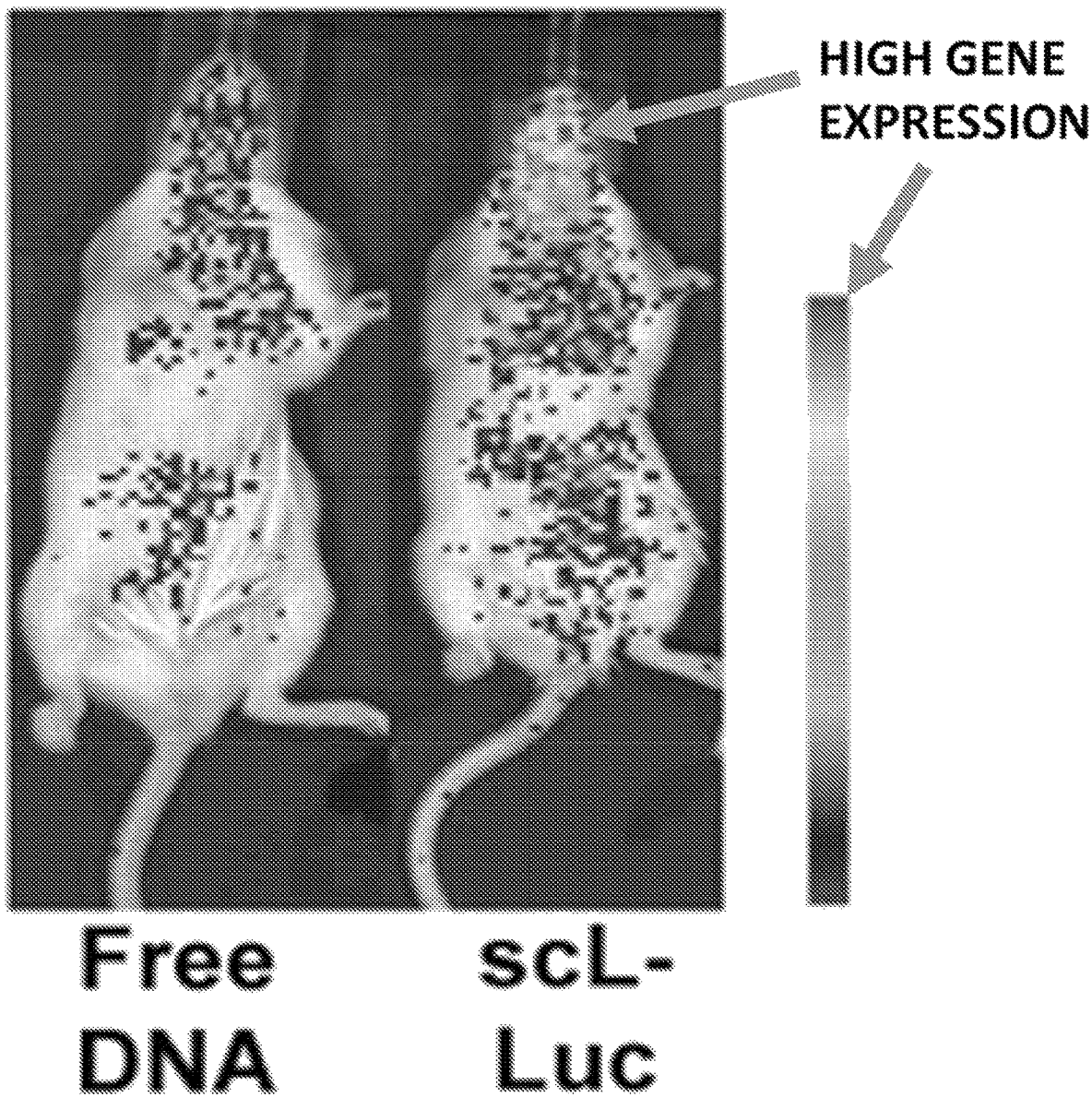
FIG. 5 shows level of expression of the luciferase gene either as Free (unencapsulated), or scL-encapsulated plasmid DNA, after intranasal administration to Balb/c mice.

Enhanced Luciferase Expression and Tissue Uptake by scL Delivery after Intranasal Administration The Luciferase gene, either as Free (unencapsulated), or scL-encapsulated plasmid DNA, prepared as described below in Example 7, was intranasally administered to Balb/c mice. 24 hours post intranasal administration the mice were intraperitoneally injected with Luciferin and imaged with a IVIS® (Xenogen) In Vivo Imaging system (Perkin Elmer). The difference in the level of gene expression is shown in FIG. 5.

In these mouse experiments the timing and level of uptake of an scL delivered reporter after intranasal administration were assessed. The scL nanocomplex prepared using the ratios disclosed above encapsulating an FITC labeled molecule (100 µg) was intranasally administered to immune competent mice. At times from 6-48 hrs post-administration, animals were humanely euthanized. Liver, lung and brain tissues were excised and subjected to Flow cytometry to determine the number of FITC positive cells in each organ at each time point. For all three organs the percent of FITC positive cells was found to peak between 16 and 30 hours. The % of cells in each tissue that were transfected at the peak time varied. Not unexpectedly, the largest % of FITC positive cells was found in the lungs (~20-40%) while 3-4% positive cells were found in the brain and ~1.5% of the liver cells carried the scL delivered molecule. However, it should be noted that, since the liver is a large organ, based upon Marino (20), 1.5% of liver cells is ~2.25×10$^7$ cells, a relatively large number. Similarly, 20-40% positive cells in the lung represents ~$5.7 \times 10^7$ cells, while 3-4% positive cells in brain equals ~$4.4 \times 10^6$ cells.

EXAMPLE 5

In Vitro Induction of ERKI/II Expression by Carbachol

Figure 6:
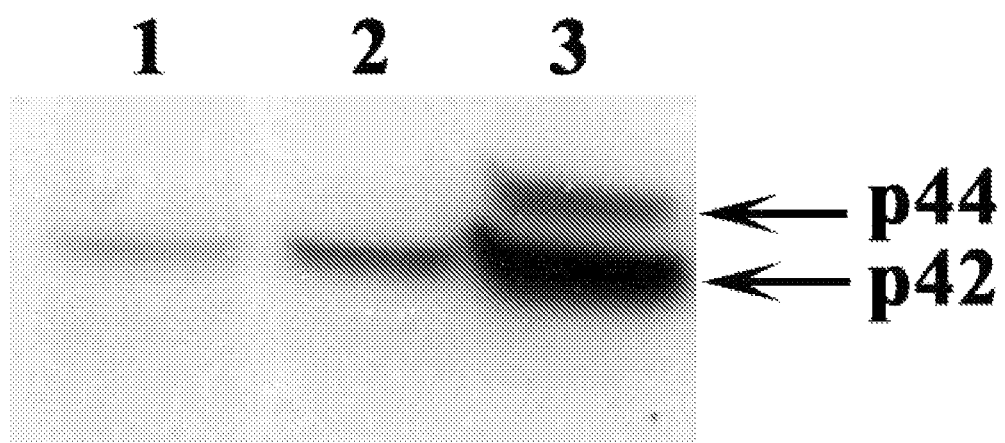
FIG. 6 shows Western analysis of total cellular protein using an antibody that detects both ERKI and ERKII proteins.

Carbachol is a drug that binds and activates the acetylcholine receptor (agonist). Thus treatment with Carbachol mimics the effects of OP agents. Carbachol has been shown to induce expression of ERKI/II in brain (21). That treatment of lung cancer cells with Carbachol can induce expression of ERKI/II and that pre-treatment with atropine, a competitive inhibitor (antagonist) of the muscarinic acetylcholine receptors can inhibit this induction (FIG. 6). Human A549 cells were used as a model to test these responses. A549, with or without 30 min pre-treatment with 100 uM atropine (final concentration), were treated with 100 µM (final concentration) Carbachol. Thirty minutes later the cells were harvested, protein isolated and 60 µg total cellular protein analyzed by Western using an antibody that detects both ERKI and ERKII proteins. Lane 1=untreated (uninduced) cells showing low basal levels of the proteins; Lane 3=Induced expression after Carbachol treatment; Lane 2=Lack of ERKI/II induction after pre-treatment with Atropine followed by Carbachol treatment. Thus, inhibition of this Carbachol induced expression of ERKI/II can be used as a downstream molecular surrogate to assess the effectiveness of scL-mtBChE/scL-ppol treatment both in vitro and in vivo.

EXAMPLE 6

Cloning into High Expression Vector pSCMV

Plasmid vectors containing either the wt human BChE (huBChE), the G117H mutant version of human BChE (mtBChE) (see, e.g., McTiernan, et al., "Brain cDNA clone for human cholinesterase," *Proc. Natl. Acad. Sci.* 84:6682-6686, FIG. 2, the disclosure of which is incorporated by reference herein in its entirety for all purposes) or a polyproline rich peptide (ppro) (see Altamirano and Lockridge, *Chemico-Biological Interactions* 119-120:53-60 (1999) (see page 57, section 2.9); Krejci et al., *The Journal of Biological Chemistry* 272:22840-22847 (1997) (see page 22842, FIG. 1); and Bon et al., The *Journal of Biological Chemistry* 272:3016-3021 (1997) (see section bridging pages 3016-3017) the disclosures of which are incorporated by reference herein in their entireties) downstream of the high expression promoter disclosed in U.S. Published Patent Application No. 2007/0065432 have been prepared. The plasmid vector (pSCMV) results in levels of expression of the gene of interest 2-10 fold higher than with standard constructs. This high expression plasmid, pSCMV, is derived from the pBR322 plasmid backbone and also contains a multiple cloning site, and a gene conferring resistance to the antibiotic Kanamycin. This plasmid has been prepared to carry two different tumor suppressor genes under cGMP condition for use in human clinical trials. Thus, the construct is acceptable to the FDA for use in humans. Using standard procedures, and restriction sites well known by those familiar with the art, the 1.8 Kb BChE and ~300 Bp ppro inserts (11) from the original vectors were subcloned into the multiple cloning site in pSCMV (FIG. 7). The resulting plasmids were propagated in commercially available bacterial host TOP 10 F[1] (Invitrogen, Carlsbad, Calif.). Plasmid DNA was then prepared using standard methods well known in the art. The resultant plasmids were tested. Analysis indicated a 260:280 ratio of >1.9, the presence of >75% supercoiled molecules in the population (FIG. 8), and undetectable levels of endotoxin.

EXAMPLE 7

In Vitro Characterization of the Clones Produced in Example 6

The pSCMV plasmids carrying either the huBChE, mtBChE or ppro genes are characterized for level of BChE activity, $T_{1/2}$ and to determine the optimum ratio of BChE to ppro for activity and tetramerization. For the studies described below a commercially available (from ATCC) cell line, CHO (Chinese hamster ovary), human lung cancer A549 or human prostate cancer DU145 cells are employed. CHO, which has a basal level of BChE activity, is used for continuity purposes since these cells were previously employed by other investigators, including Lockridge and collaborators, in the study of BChE activity (11).

Assessing Level of BChE Expression

The pSCMV-wtBChE or the pSCMV-mtBChE vectors are encapsulated in the scL nanocomplex together with the pSCMV-ppro vector to form scL-wtBChE/ppro and scL-mtBChE/ppro complexes. The vectors are mixed for encapsulation at a 4:1 molar ratio (pSCMV-mtBChE to pSCMV-ppro) of the inserts. The ratios of TfRscFv ligand, liposome and total plasmid DNA are 0.33 ug to 10 ug to 1 ug (TfRscFv to liposome to DNA). The complex is formed by simple mixing of components at a defined ratio (32).

Exemplary liposome components

| | | |
|---|---|---|
| LipA | DOTAP/DOPE | 1:1 molar ratio |
| LipB | DDAB/DOPE | 1:1 molar ratio |
| LipC | DDAB/DOPE | 1:2 molar ratio |
| LipD | DOTAP/Chol | 1:1 molar ratio |
| LipE | DDAB/Chol | 1:1 molar ratio |
| LipG | DOTAP/DOPE/Chol | 2:1:1 molar ratio |
| LipH | DDAB/DOPE/Chol | 2:1:1 molar ratio |

(DOTAP = dioleoyltrimethylaminnonium phosphate, DDAB = dimethyldioctadecylammonium bromide; DOPE = dioleoylphosphatidylethanolamine; chol = cholesterol).

Liposomes are prepared by the ethanol injection method modified from that described by Campbell, M J (Biotechniques 1995 Jun. 18(6):1027-32). In brief, all lipids are solubilized in ethanol and mixed, injected into vortexing pure water of 50-60° C. with a Hamilton syringe. The solution is vortexed for a further 10-15 min. The final concentration is 1-8 mM total lipids.

The TfRscFv-immunoliposome complexes (other ligands can also be used as described herein) are prepared by mixing the TfRscFv with liposome composition A (or any of the liposome compositions given above) at defined ratios of single chain protein to liposome and DNA in the mixed complex. The preparation of the complexes is in accordance with the following general procedure.

The appropriate amount of 2 mM to 8 mM liposome (A-H described above) is mixed with any water (e.g., DI water) required to give a desired volume and gently inverted 10 times to mix, or for larger volumes rotated at 20-30 RPM for 1-2 minutes. To the liposome-water mixture, the appropriate amount of TfRscFv, antibody or antibody fragment is added to give the desired ratio and mixed by gentle inversion for about 5-10 seconds or for larger volumes rotated at 20-30

RPM for 1-2 minutes. This mixture is kept at room temperature for 10-20 minutes (again inverted gently for 5-10 seconds after approximately 5 minutes). At the same time, the appropriate amount of DNA comprising the, the pSCMV-wtBChE vector, or pSCMV-mtBChE vector and pSCMV-ppro vector constructs (at a molar ratio of the BChE to ppro inserts of 10:1 to 1:10, more preferably 5:1 to 1:5, most preferably 4:1, 2:1 or 1:1) is mixed by inversion for 5-10 seconds, or for larger volumes rotated at 20-30 RPM for 1-2 minutes, with any water required to give a desired volume. Typically, for in vivo use, it is desirable to provide about 5 μg to about 100 mg of DNA per administration (includes IN, oral, Aerosol, IV, IP, IM etc).

The DNA solution is quickly added to the TfRscFv (or antibody or antibody fragment)-liposome solution and the mixture is inverted for 5-10 seconds or for larger volumes rotated at 20-30 RPM for 1-2 minutes. The final mixture is kept at room temperature for 10-20 minutes, gently inverting again for 5-10 seconds after approximately 5 minutes. For use in vivo, 50% dextrose or 50% sucrose is added to a final concentration of 5-20% (V:V) and mixed by gentle inversion for 5-10 seconds, or for larger volumes rotated at 20-30 RPM for 1-2 minutes. A specific example at a suitable ratio (w:w) of TfRscFv to Liposome to DNA of 0.33 μg to 10 μg to 1 μg is as follows. For 40 μg of total DNA in a final volume of 800 mix 183 μl water with 280 μl of 2 mM liposome solution. Add 34 μl of TfRscFv (with a concentration of 0.4 μg/ml). Mix 183 μl water with 40 μl of 1 μg/1 μl DNA. Add 80 μl of 50% Dextrose or 160 μl of 50% Sucrose as the last step.

When the {K[K(H)KKK]5-K(H)KKC} peptide (HoKC) (SEQ ID NO: 1) is included in the complex, the cationic liposomal formulations A (DOTAP:DOPE at a 1:1 molar ratio), B (DDAB:DOPE at 1:1), G (DOTAP:DOPE:cholesterol at 1:1:1) and H (DDAB:DOPE:cholesterol at 1:1:1) (or any of the liposomes formulations given above) are prepared using the ethanol injection method as described above. Each liposome formulation also includes MPB-DOPE at 5 molar percent of total lipid. Since the HoKC peptide carries a terminal cysteine, MPB-DOPE is included in all of the liposome compositions to allow conjugation of peptide to the liposome. The Lip-HoKC liposomes are prepared using a coupling reaction between the cationic liposomes carrying the maleimide group (Lip-MPB) and the peptide as follows. An aliquot of 0.1 mmol of the peptide with a free thiol group on cysteine is added to 2 mmol of Lip-MPB in 10 mM HEPES, pH 7.4, solution and rotated at room temperature (20-30 r.p.m.) for 2 h. The resulting Lip-HoKC has a lipid concentration of 1.4 mM.

When the liposome comprises HoKC, the full complex is formed in a manner identical to that used to produce the TfRscFv-Lip-DNA complex without HoKC. Here also the TfRscFv or any antibody or antibody fragment (including Fab' or Mab) is mixed with Lip-HoKC (by gently inversion 10 times or for larger volumes rotated at 20-30 RPM for 1-2 minutes) at a specific ratio, and incubated at room temperature for 10-20 min. DNA is then added to the TfRscFv (or antibody or antibody fragment)-Lip-HoKC solution, mixed by gently inversion 10 times or for larger volumes rotated at 20-30 RPM for 1-2 minutes, and again incubated at room temperature for 10-20 min, after which dextrose or sucrose is added to a final concentration of 5-20%, mixed by gentle inversion 10 times, or for larger volumes rotated at 20-30 RPM for 1 minute, and incubated at room temperature for 10-20 minutes. The ratio of the TfRscFv:LipA-HoKC:DNA in the complex is 0.3 mg:7 nmol:1 mg.

Dynamic Laser Light Scattering (DLS) with a Malvern Zetasizer NanoZS is employed to measure the size of the scL nanocomplexes. The size of the complex suitably is less than 400 nm. This instrument also has the capability to measure zeta-potential, a determinant of the overall charge of the nanocomplex. For these complexes the charge is suitably positive, between about 20 and 50 mV. Modifying the ratios of the components to control the size, charge and/or activity of the scL-wtBChE/ppro or scL-mtBChE/ppro can readily be carried out as desired.

The sizes of the nanocomplexes prepared as described above are shown in Table 2

| | Size | Molar Ratio (BChE to ppro) |
|---|---|---|
| scL-pSCMV wtBChE | 114.7 nm | — |
| scL-pSCMV mtBChE | 134.5 nm | — |
| scL-CMV mtBChE | 105.3 nm | — |
| scL-pSCMV mtBChE/ppro | 105.1 nm | 2:1 |
| | 96.4 nm | 4:1 |
| scL-CMV mtBChE/ppro | 97.1 nm | 2:1 |
| | 72.1 nm | 4:1 |

The Zeta potentials were in the range of 20-40.

CHO cells, DU145 or A549 cells are plated at ~$2\times10^5$ cells/well of a 6 well plate or $2\times10^4$ cells/well of a 24 well plate. The total DNA dose for transfection in these initial experiments is 0.1 to 2 μg/well. This dose is based upon prior transfection experience which has shown that this dose is often the most appropriate when transfecting this number of cells. 24 hrs later the cells are transfected with the scL-wtBChE/ppro or the scL-mtBChE/ppro complexes prepared using the method as described above. The CHO cells are also transfected with scL encapsulating the original vector constructs which have the unmodified CMV or RSV promoters to serve as controls. Untransfected cells are also included in all experiments. Based upon previous experience with the pSCMV plasmid, there is significant protein expression within 24 hours. Thus, ~24 hours post-transfection the relative amounts of BChE tetramers, dimers and monomers in each of the samples (in both the cells and the supernatant) are assessed by non-denaturing polyacrylamide gel electrophoresis on 4-30% gradient gels and staining with 2 mM butyrylthiocholine by the method of Karnovsky and Roots (23, 33). Purified plasma huBChE is included as a control. At least a 2 fold increase in BChE protein detected after transfection is considered a positive result.

Examples of the results of such experiments are shown in FIGS. 9-11. CHO cells or A549 cells were plated at ~$2\times10^4$ cells/well of a 24 well plate. The scL nanocomplex was prepared encapsulating a plasmid encoding the mutant BChE plus a second plasmid encoding the ppro gene. In these plasmids the gene was under the control of a standard cytomegalovirus (CMV) promoter or under the control of the high expression vector (pSCMV) described in this application.

In the experiments with the CHO-K1 cells, the complexes were prepared using the method as described above. The total DNA in each scL nanocomplex was 1 ug/well in 30 ul For the scL nanocomplex encapsulating the vector carrying the mtBChE gene under the control of the pSCMV promoter and the and the vector carrying the ppro gene under the control of the pSCMV promoter, 22.4 μl of 2 mM liposome solution was added to 63.5 ul water. The liposome-water was mixed with 5.08 μl of TfRscFv (with a concentration of 0.34 μg/ml). To the cationic liposome-TfRscFv mixture was added 3.2 µg of total DNA (the specific BChE plus ppro vectors) in a final volume of 5.02 µl. Of the final scL nanocomplexes 3, 9 or 18 ul (representing 0.1, 0.3 and 0.6 ug total DNA, respectively) of the scL nanocomplexes were added to the cells.

Figure 9:
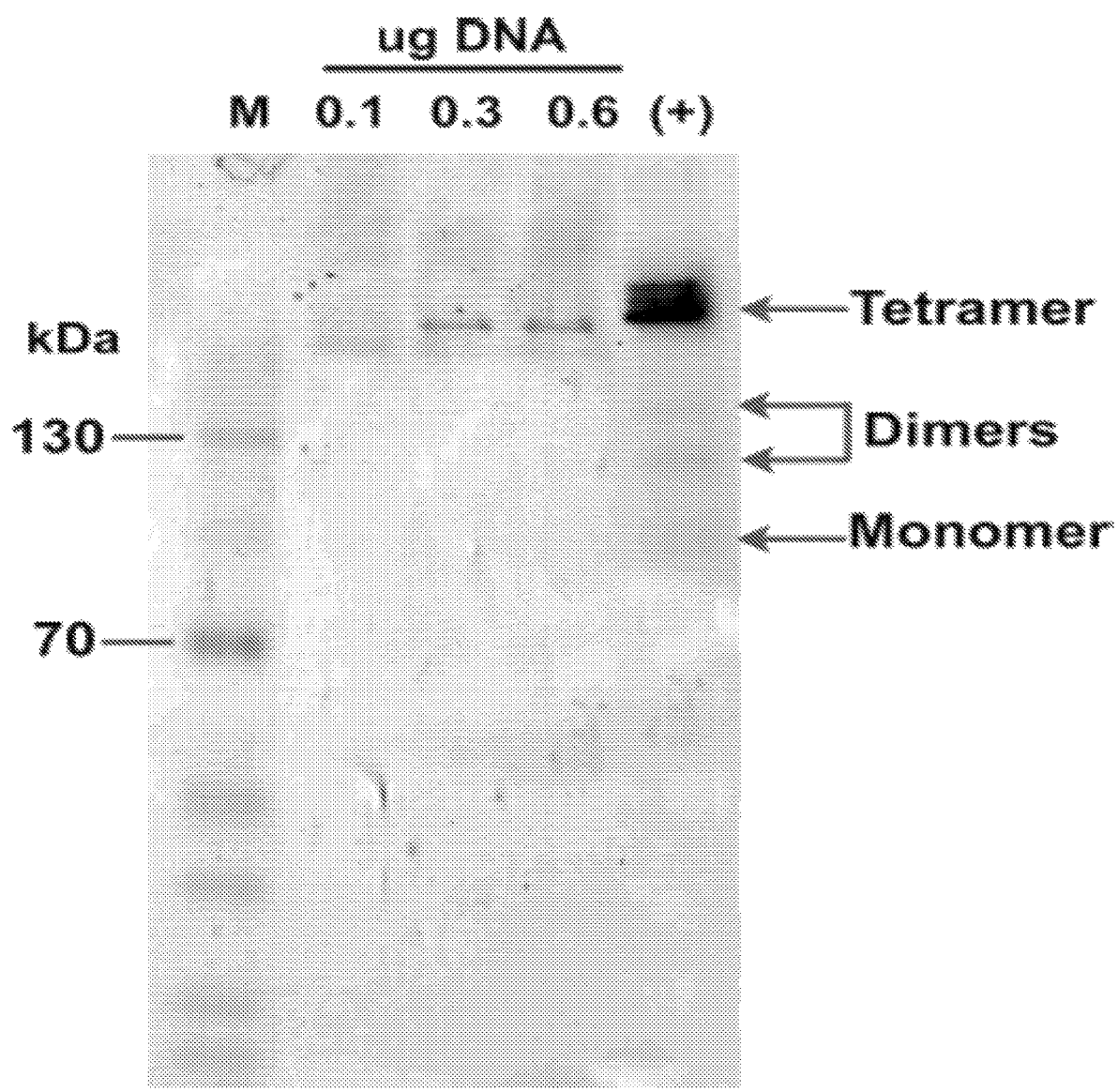
FIG. 9 shows the level of expression of BChE in CHO-K1 cells after transfection with increasing amounts of DNA in the scL-mtBChE/ppro complex.

In these experiments the molar ratio of the BChE plasmid DNA to the ppro plasmid DNA was 4:1. The expression of exogenous BChE was assessed by non-denaturing polyacrylamide gel electrophoresis on 4-30% gradient gels and staining with 2 mM butyrylthiocholine by the method of Karnovsky and Roots (23, 33). As shown in FIG. 9 with CHO-K1 cells transfected with scL-mtBChE/ppro nanocomplex, there is a DNA dose dependent increase in expression of the BChE evident. Unexpectedly, nearly 100% of the BChE was present in the active Tetramer form.

A549 cells were transfected with either scL-CMV mtBChE/ppro or scL-pSCMV mtBChE/ppro prepared using the method as described above. For the scL nanocomplex encapsulating the vector carrying the mtBChE gene under the control of the CMV promoter and the and the vector carrying the ppro gene under the control of the CMV promoter, or the scL nanocomplex encapsulating the vector carrying the mtBChE gene under the control of the pSCMV promoter and the and the vector carrying the ppro gene under the control of the pSCMV promoter 14 µl of 2 mM liposome solution was added to 32.83 ul water. The liposome-water was mixed with 3.17 µl of TfRscFv (with a concentration of 0.21 µg/ml). To the cationic liposome-TfRscFv mixture was added 3.2 µg of total DNA (the specific BChE plus ppro vectors) in a final volume of 10.19 (CMV promoter) or 31.39 µl (pSCMV promoter). Enough Serum Free Media was added to bring the final volume to 100 ul. Of the final scL nanocomplexes 25 ul (representing 0.5 ug total DNA) of the scL nanocomplexes was added to the cells. In these experiments the molar ratio of the BChE plasmid DNA to the ppro plasmid DNA was 4:1.

Figure 10:
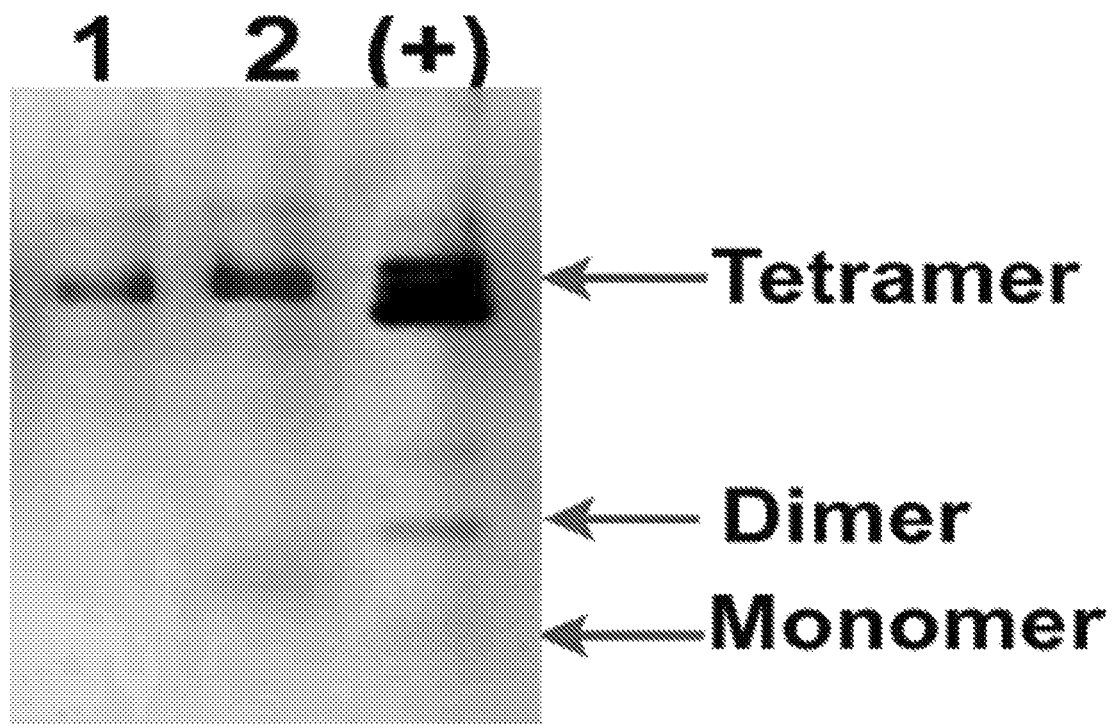
FIG. 10 shows BChE Expression 16 days after In Vitro Transfection of A549 Cells with scL-mtBChE/ppro complex.
Figure 11:
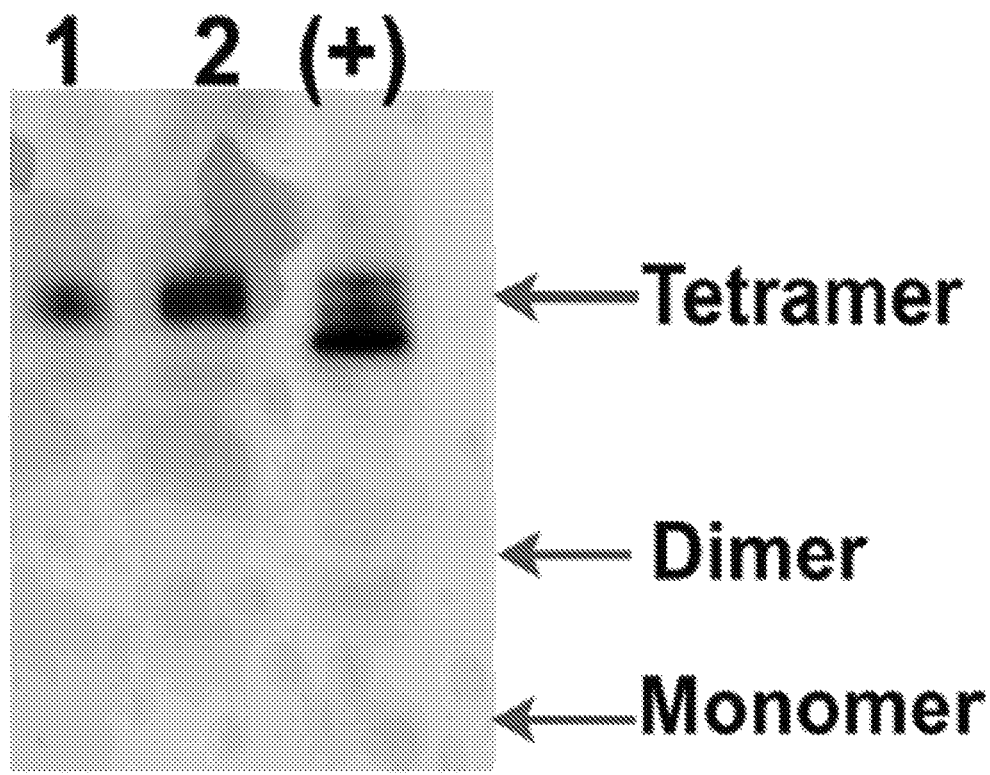
FIG. 11 shows BChE Expression 28 days after In Vitro Transfection of A549 Cells with scL-mtBChE/ppro complex.

The level of BChE expression with each of the scL complexed plasmids was assessed at two time points by non-denaturing polyacrylamide gel electrophoresis on 4-30% gradient gels and staining with 2 mM butyrylthiocholine by the method of Karnovsky and Roots (23, 33). As shown in FIG. 10 (16 days post-transfection) and FIG. 11 (28 days post-transfection), at both time points there is a significantly higher level of BChE expression in the cells transfected by the scL carrying the BChE and ppro under control of the high expression pSCMV promoter compared to those transfected with the plasmids under control by standard CMV promoter. Unexpectedly, this increase in expression is even greater as time goes on (28 days).

Assessing Level of BChE Activity

Transfection of CHO DU145 and A549 cells with scL-wtBChE/ppro, or scL-mtBChE/ppro, with the plasmids under the control of either the high expression pSCMV promoter or the standard CMV promoter, and with the controls described above, are performed. 24 hours post-transfection, the level of BChE activity in the cells and supernatant is determined by means of the Ellman assay (34,35). BChE activity is determined with 1 mM butyrylthiocholine in 0.1M potassium phosphate, 0.5 mM dithiobisnitrobenzoic acid at 25° C., monitoring absorbance at 412 nm. Functional activity is calculated using the molar extinction coefficient of 13,600 $M^{-1}$ $cm^{-1}$. These experiments are designed to confirm the increased activity of mt over wt BChE clones while in the pSCMV vectors, analogous to the previously reported findings with the original unmodified vectors (10,11). At least a 2 fold increase in BChE activity with the pSCMV-mtBChE clone as compared to the pSCMV-wt BChE clone is desirable.

Examples of such experiments in DU145 cells are shown below. Different molar ratios of the pSCMV plasmid DNAs encoding mtBChE to the pSCMV plasmid DNAs encoding ppro in the scL nanaocomplex were performed in DU145 cells. In these experiments molar ratios of 2:1 (Table 3) and 4:1 (Table 4) were used. 2.5×$10^4$ DU145 cells were seed/well of a 24 well plate and were transfected 24 hours later. The scL nanocomplexes were prepared using the same ratio of 0.33 ug TfRscFv to 10 ug Liposome to 1 ug total DNA using the procedure described above in Example 7. For each of the scL nanocomplexes, 2 μg of total DNA (pSCMV-BChE and pSCMV-ppro at the appropriate ratios) in a final volume of 5.3 μl (with additional 1×Tris:EDTA buffer as needed to make 5.3 ul) was used. To 3.17 μl of TfRscFv (with a concentration of 0.34 μg/ml) was added to 4.7 ul water and 14 μl of 2 mM liposome. To this TfRscFv-Liposome mixture was added the 5.3 ul of DNA from above. 3 ul of Serum Free Medium was added and the resulting mixed by gentle inversion prior to addition to the cells. The total DNA in each scL nanocomplex was 0.5 ug/well in 25 ul. The levels of BChE activity assessed by Ellman assay is shown below in Tables 3 and 4.

TABLE 3

Transfection of DU145 Cells 0.5 ug DNA (mtBChE:ppro Ratio = 2:1):

| Days Post-Transfection | CONSTRUCT | ACTIVITY (U/mL × $10^{-3}$) |
|---|---|---|
| 5 | scL-CMV | 1.51 |
| | scL-pSCMV | 2.15 |
| 7 | scL-CMV | 2.96 |
| | scL-pSCMV | 3.68 |
| 9 | scL-CMV | 4.49 |
| | scL-pSCMV | 5.38 |

TABLE 4

Transfection of DU145 Cells 0.5 ug DNA (mtBChE:ppro Ratio = 4:1):

| Days Post-Transfection | CONSTRUCT | ACTIVITY (U/mL × $10^{-3}$) |
|---|---|---|
| 13 | scL-CMV | 1.367 |
| | scL-pSCMV | 1.416 |
| 18 | scL-CMV | 1.175 |
| | scL-pSCMV | 1.342 |

At both ratios, the level of BChE activity is higher after transfection when the genes are cloned into the high expression promoter then when they are under the control of the standard CMV promoter showing the difference between this approach and that currently in use by others in the field.

After confirming that the mtBChE clone has higher activity than wt, only the mtBChE clone is employed in additional experiments. After confirming that the genes cloned into the constructs under the control of the high expression promoter have higher activity than when under the control of the standard CMV promoter, only the these clones are employed in additional experiments.

Determining Optimal Molar Ratio

The molar ratio of the pSCMV-mtBChE insert to pSCMV-ppro insert in the scL complex for transfection of the CHO and/or A549 cells is varied to establish the ratio that results in the highest amount of tetramers and activity. The molar ratios (pSCMV-mtBChE to pSCMV-ppro) are 4:1; 1:1 and 1:4. 24 hours post-transfection, the cells and supernatant are harvested and the activity determined via the Ellman assay. The relative amount of tetramers, dimers and monomers are assessed via non-denaturing gel electrophoresis as described above. It is desirable that the scL-mtBChE/ppro inserts yield at least 40%, more suitably 70%-90% of the tetramer form. Modification of the ratios can be utilized to achieve a desired level of tetramers.

Experiments using different molar ratios of the pSCMV plasmid DNAs encoding mtBChE to the pSCMV plasmid DNAs encoding ppro in the scL nanaocomplex were performed in DU145 cells. In these experiments molar ratios of 2:1, 1:1 or 1:2 (BChE:ppro) (Table 5) were used. $2.5 \times 10^4$ DU145 cells were seed/well of a 24 well plate and were transfected 24 hours later. The scL nanocomplexes were prepared using the same ratio of 0.33 ug TfRscFv to 10 ug Liposome to 1 ug total DNA using the procedure described above in Example 7. To 1 µl of TfRscFv (with a concentration of 0.34 µg/ml) was added 10 ul water. To this was added 7 µl of 2 mM liposome solution. For each of the scL nanocomplexes, 1 ng of total DNA (pSCMV-BChE and pSCMV-ppro at the appropriate ratios) in a final volume of 5 µl was mixed with 15 ul of water then added to the TfRscFv-liposome solution. 62 ul of Serum Free Medium was then added and the resulting mixed by gentle inversion prior to addition to the cells. The total DNA in each scL nanocomplex was 0.3 ug/well in 30 ul.

TABLE 5

Transfection of DU145 Cells at Different Ratios of pSCMV-BChE to pSCMV-ppro in the scL Nanocomplex:

| Days Post-Transfection | RATIO (BChE/ppro) | ACTIVITY (U/mL × $10^{-3}$) |
| --- | --- | --- |
| 12 | UT | 6.41 |
|  | 2:1 | 6.49 |
|  | 1:1 | 7.35 |
|  | 1:2 | 7.03 |
| 19 | UT | 5.63 |
|  | 2:1 | 6.57 |
|  | 1:1 | 5.98 |
|  | 1:2 | 5.61 |

Determining Peak and Duration of Expression/Activity

Based upon previous experience with the pSCMV plasmid, significant protein expression begins ~24 hours post-transfection and continues for up to 4-5 days. Thus, to determine the time of peak BChE expression and activity, CHO and/or A549 cells are transfected with scL-mtBChE/ppro prepared at the desired molar ratio. Daily from days 0 (pre-treatment) to 14 post-transfection the cells and supernatant are harvested, and the level of BChE activity determined via Ellman assay. A significant increase in the relative amount of the tetrameric form of BChE and an activity curve and $T_{1/2}$ similar to that of normal hBChE is desired. mtBChE activity from between 1 to 14 days or even longer is desirable. The results of experiments described above in Examples 7 (FIGS. 10 and 11 and Tables 3-5) demonstrate an increase in expression of the tetrameric form of BChE and the activity of BChE over time using the scL nanocomplex of this application.

EXAMPLE 8

Assessing Efficacy In Vitro

Carbachol is a drug that binds and activates the acetylcholine receptor (agonist). Thus, treatment with Carbachol mimics the effects of OP agents. As the use of chemical warfare agents is strictly regulated, Carbachol can be used as a nerve agent model compound. Carbachol induced the expression of ERKI/II in human lung cancer A549 cells, and this induction is reversed by pre-treatment with the muscarinic receptor antagonist atropine (FIG. 6). In this Example, the ability of transfected scL-mtBChE/ppro to protect against OPs in vitro, using expression of ERKI/II as the surrogate end-point, is investigated.

A549 cells are transfected with scL-mtBChE/ppro at the desired ratio. At the peak expression/activity time, the cells are treated with 100 µM Carbachol. 30 min later the cells are harvested and ERKI/II expression levels determined by Western analysis. Untreated cells and those treated only with Carbachol, or just scL-mtBChE/ppro serve as controls. The cells are harvested, and protein isolated as previously described (13). 40 µg of total protein is separated by SDS PAGE electrophoresis, transferred to a Nylon membrane and probed with an antibody that detects both ERKI and ERKII proteins, and a signal is detected using the ECL Western blotting detection system (GE Lifesciences)

Prophylactic treatment with the scL-mtBChE/ppro suitably inhibits the Carbachol induced expression of ERKI/II. Various doses of the scL nanocomplexes are tested to achieve maximum inhibition which is at least 50%, more preferentially 70%, most preferentially 90% or greater. If at least 50% inhibition is not observed, the dose of the scL is suitably increased (no change in ratio) until it is achieved. Moreover, at the time of Carbachol treatment, a portion of the cells and supernatant are used to determine the level of BChE activity by the Ellman assay to correlate activity with down-modulation of ERKI/II.

EXAMPLE 9

Establishing Baseline BChE Levels in Mice

A transgenic homozygous BChE knockout mouse (BChE−/−) as a model for human BChE deficiency has been developed (29) and is commercially available from Jackson Laboratories. These mice are in a C57BL/6 background (BChE+/+). Thus, using published procedures well known in the art (29), the baseline level of BChE activity in plasma, lung, brain and liver tissues is determined by the Ellman assay in the BChE−/− knockout and in C57BL/6 mice. The baseline activity of BChE in the plasma, lung, brain and liver in the BChE knockout mouse (BChE−/−) is suitably in the range of 0+0.005, 0.01+0.02, 0.02+0.02 and 0.09+0.05 U/ml (plasma and U/mg (tissues), respectively. The baseline activity of BChE in the plasma, lung, brain and liver in the C57BL/6 mice (BChE+/+) is suitably in the range of 1.5+0.3, 0.38+0.2, 0.2+0.1 and 3.0+0.5 U/ml (plasma and U/mg (tissues), respectively.

The levels of BChE activity in the plasma of normal, untreated C57BL/6 mice (BChE+/+) was assessed by the Ellman Assay as described above using well established protocols know in the literature (34, 35). Two individual mice were tested. The background level of BChE was found to be 0.014+0.0009 U/ml (Mean±Std Error).

EXAMPLE 10

Establishing Baseline Response of Mice to Carbachol

C57BL/6 mice are used to establish the dose of Carbachol that results in an at least a 2 fold increase of ERKI/II expression over baseline level. Carbachol at doses of 0.15, 0.55 or 1.5 umol/Kg (36) are i.p. administered to 9-12 wk old female C57BL/6 mice, 5 mice/dose. 30 minutes post administration, the mice are humanely euthanized and lung, brain and liver removed, protein isolated and the level ERKI/II expression determined as described herein. The dose of Carbachol (0.15 to 1.5 umol/Kg, more preferably 0.55 umol/Kg) that yields at least a 2 fold increase in ERKI/II expression, and does not result in overt toxicity to the mice, is desired.

EXAMPLE 11

In Vivo Studies in Homozygous Negative BChE Knockout Mice (BChE$^{-/-}$)

As the homozygous negative knockout mice are virtually devoid of BChE activity, they are a good model in which to confirm the optimal molar ratio of pSCMV-mtBChE to pSCMV-ppro in the scL complex, the dose to be administered and the resulting duration and peak expression of the IN administered complex for in vivo use.

A total of 3 ratios surrounding and including the optimal molar ratio of pSCMV-mtBChE to pSCMV-ppro determined in vitro are assessed for BChE activity by the Ellman assay. The scL complex prepared at the different ratios is administered via IN inoculation of 9-12 wk old female BChE−/− mice (15 mice/group). Untreated mice serve as controls. As the $T_{1/2}$ of human plasma BChE is 11-14 days, 2 mice are euthanized from each group every other day from day 0 (pre-treatment) today 14 and the level of BChE activity in plasma at each time point assessed by the Ellman assay to determine the time course and peak of activity. In addition, the relative amount of tetramers, dimers and monomers in plasma is assessed via non-denaturing gel electrophoresis as described herein to correlate with activity. The ratio of between 10:1 and 1:10 (molar ratio of inserts of pSCMV-mtBChE to pSCMV-ppro), more preferentially 5:1 to 1:5, most preferentially 4:1, that yields the longest lasting and highest BChE activity is used to find the optimal in vivo DNA dose. The optimal time of expression is between days 4 to 11.

Using the optimal ratio, the DNA dose IN administered via the scL nanocomplex is varied. Initially, 3 doses are tested: 100, 75 and 50 ug total DNA. The scL-mtBChE/ppro complex, prepared as described herein, is administered at the specified DNA dose via IN inoculation of 9-12 wk old female BChE−/− mice (15 mice/dose). Untreated mice serve as controls. The scL-mtBChE/ppro nanocomplex is administered in a total volume of 50 to 400 μL. Unanesthetized mice are held along the back in the palm of the hand. Holding the mice with the head tilted downward at an approximate 30 degree angle, 10 uL of the nanocomplex is slowly dripped into the nostril of the animal. The animal is allowed to rest for a period of 30 to 60 seconds before an additional 10 μL is administered in the alternate nostril. This proceeds until the entire solution is administered. For volumes over 100 uL, the animals receiving the solutions are alternated after each 100 μL to permit more time between administrations for less stress on the mice. At the peak expression time determined above, the animals are humanely euthanized and the level of BChE activity in plasma with each DNA dose determined by Ellman assay. In addition, the relative amount of tetramers, dimers and monomers in plasma with each DNBA dose are assessed via non-denaturing gel electrophoresis as described herein. The optimal DNA dose gives at least 500 U/ml BChE activity in plasma and results in at least 40%, more preferably 70%-90% tetramer form.

EXAMPLE 12

Assess Activity of Exogenous mtBChe in BChE$^{+/+}$ Mice

As this strain of mice is BChE$^{+/+}$, this model is more analogous to the human population. The optimal dose/ratio of the DNA in the scL-mtBChE/ppro complex is administered via IN inoculation of 9-12 wk old female C57BL/6 mice (20 mice/group) as described herein. Untreated mice serve as controls. At the peak expression time, the animals are humanely euthanized and the level of BChE activity in plasma, determined by Ellman assay. In addition, the relative amount of tetramers, dimers and monomers in plasma is assessed via non-denaturing gel electrophoresis as described herein. A level of BChE activity at least 2 fold greater than the endogenous baseline level is desired.

EXAMPLE 13

In Vivo Efficacy Studies

In these studies four groups of normal C57BL/6 mice are used: Group 1=Untreated control; Group 2=Carbachol treatment alone; Group 3=IN treatment with scL-mtBChE/ppro nanocomplex only; Group 4=IN treatment with scL-mtBChE/ppro nanocomplex followed by Carbachol treatment. The optimal DNA dose in the scL complex at the optimal ratio of the pSCMV-mtBChE to pSCMV-ppro vectors, (prepared as described herein) is IN administered (as described herein) to 9-12 wk old female C57BL/6 mice (10 mice/group). At the time of BChE peak expression, the animals in groups 2 and 4 receive (i.p.) the optimal dose of Carbachol (0.15 to 1.5 μmol/Kg, more preferably 0.55 μmol/Kg). Thirty minutes after Carbachol administration, the mice are humanely euthanized and the level of BChE activity in plasma assessed by the Ellman assay. ERKI/II expression is also examined by Western analysis, in lung, brain and liver tissues to correlate activity with down-modulation of ERKI/II. Body weight of mice is measured to look for signs of toxicity from the scL-mtBChE/ppro complex. Carbachol, a muscarinic agonist, has been shown to stimulate muscarinic acetylcholine receptor (mAChR) and activate ERKI/II, which have been shown to act as a convergence site for various extracellular signals, including mAChR activation. Prophylactic treatment with the scL complexes suitably results in the inhibition of the Carbachol induced expression of ERKI/II. A least 50% inhibition of ERKI/II is desired. DNA dose in the scL complex is suitably modified (no change in ratio) until it is achieved. Alternatively, multiple administrations, every 3rd day to a total of 3 administrations, prior to treatment with Carbachol can be given.

EXAMPLE 14

Prophylactic Use of scL-mtBChE/Ppro as an Anti-OP Agent in Mice

The extent and duration of protection offered by IN administered scL-mtBChE/ppro nanocomplex is determined in mice by challenge with escalating doses of echothiophate (Wyeth-Ayerst), which is a chemical warfare nerve agent-simulating compound. Challenge experiments with echothiophate are performed using wild-type strain C57BL/6 mice (BChE+/+) mice. scL-mtBChE/ppro at doses of 50-100 μg total pSCMV-mtBChE/pSCMV-ppro DNA (at the preferred molar ratio of the inserts (10 to 1 to 1:10 [mtBChE to ppro], more preferably 5:1 to 1:5, most preferably 4:1) is IN administered as described herein. A group of mice do not receive the scL-mtBChE/ppro nanocomplex. Plasma is collected from all mice before IN administration and at the indicated intervals through day 11-21 post scL-mtBChE/ppro administration for assay of BChE activity. On the day of peak activity (day 4 to 11) post IN administration baseline temperature, body weights and observations are recorded. Mice are challenged subcutaneously with $2 \times LD_{50}$ of echothiophate (200 ug/kg). Mice are observed continuously through 1 h after echothiophate challenge. Axial body temperatures and signs of cholinergic toxicity (straub tail, hunched posture, and tremors) are observed periodically through toxicant postchallenge. Moribund mice are euthanized immediately. Animals that survive the first $2 \times LD_{50}$ challenge are challenged with another $2 \times$ or $3 \times LD_{50}$ 3 h after the first challenge. Animals that survive the combined $4 \times$ or $5 \times LD_{50}$ doses of echothiophate are injected several hours later with additional $LD_{50}$ doses following the same procedures.

Control mice are expected to die within a few minutes after the first $2 \times LD_{50}$ dose of echothiophate, whereas animals that receive scL-mtBChE/ppro are expected to survive a cumulative dose of echothiophate of at least $2 \times LD_{50}$. The mice that express the highest level of mtBChE in the plasma at the time of the first challenge with echothiophate are expected survive the highest level of echothiophate challenge. Correlation between tolerated $LD_{50}$ dose and plasma BChE levels at challenge are expected.

EXAMPLE 15

Use of scL-mtBChE/Ppro for
Prophylaxis/Treatment Before and after Exposure
to OP Nerve Agents in Humans The two pSCMV plasmid DNAs are mixed during preparation of the nanocomplex at molar ratios (BChE to ppro) of the inserts of 10:1 to 1:10, more preferably 5:1 to 1:5, most preferably 4:1. The nanocomplex is suitably made at ratios of 0.33 ug:10 ug:1 ug (TfRscFv:Lip:DNA), with 5-20% Dextrose or Sucrose as an excipient when HoKC is not a component of the complex; and at ratios of 0.3 mg:7 nmol:1 mg (TfRscFv:Lip-HoKC:DNA) with 5-20% Dextrose or Sucrose when the complex comprises HoKC. The total amount of DNA in the complex is 0.01 to 10 mg/kg/administration.

The size of the final complexes prepared by these methods are suitably between about 50 and 500 (nm) with a positive zeta potential (10 to 50 mV) as determined by dynamic light scattering using a Malvern ZETASIZER® NANO-ZS. This size is small enough to efficiently pass through the pulmonary epithelium and enter the circulation and to cross the blood brain barrier.

The complex, prepared as above, is suitably used as either a prophylactic or a therapeutic agent. For prophylaxis, the ligand-targeted cationic liposome nanocomplex as prepared above is administered into humans through a number of routes, preferentially, inhalation, intranasal, oral, sublingual, etc. The ligand-targeted cationic liposome nanocomplex as prepared above can also be administered via other routes such as IM, IV, IP, ID etc.

For prophylaxis, the nanocomplex can be self administered once at least 6 hours, and suitably at approximately 24 to 48 hours, prior to exposure to a nerve agent to produce an effective amount of BChE nerve agent neutralizing enzyme to protect against at least $1 \times LD50$, and up to $5 \times LD_{50}$, of the nerve agent (including pesticides). It can also be self administered on a regular basis (once or twice weekly) for at least 3 months prior to any potential exposure to toxic nerve agents (including pesticides). The preferred methods of self-administration are via inhalation, intranasal, oral, sublingual, etc, but other methods of self-administration such as IM, IV, IP, ID etc can also be employed.

For therapeutic use, the scL-BChE/ppro nanocomplex can be administered, either self-administered or administered by another individual, anytime after exposure to nerve agents (including pesticides) starting immediately post-exposure. The nanocomplex can be administered in conjunction with other therapeutic agents and can be repeatedly administered (as often as every 24 hours) as long as medically necessary.

REFERENCES

1. Jokanovic, M. (2009). Medical treatment of acute poisoning with organophosphorus and carbamate pesticides. Toxicology Letters, 190, 107-115.
2. Maynard, R. L. & Beswick, F. W. (1992). Organophosphorus compounds as chemical warfare agents. In B. Ballantyne & T. C. Marrs (Eds.), Clinical and Experimental Toxicology of Organophosphates and Carbanates. (pp. 373-385). Butterworth: Oxford.
3. Ashani, Y. & Pistinner, S. (2004). Estimation of the upper limit of human butyrylcholinesterase dose required for protection against organophosphates toxicity: a mathematically based toxicokinetic model. Toxicological Sciences, 77, 358-367.
4. Masson, P. & Lockridge, O. (2010). Butyrylcholinesterase for protection from organophosphorus poisons: catalytic complexities and hysteretic behavior. Archives of Biochemistry & Biophysics, 494, 107-120.
5. Li, H., Schopfer, L. M., Masson, P., & Lockridge, 0. (2008). Lamellipodin proline rich peptides associated with native plasma butyrylcholinesterase tetramers. Biochemical Journal, 411, 425-432.
6. Saxena, A., Sun, W., Dabisch, P. A., Hulet, S. W., Hastings, N. B., Jakubowski, E. M. et al. (2011). Pretreatment with human serum butyrylcholinesterase alone prevents cardiac abnormalities, seizures, and death in Gottingen minipigs exposed to sarin vapor. Biochemical Pharmacology, 82, 1984-1993.
7. Aurbek, N., Thiermann, H., Eyer, F., Eyer, P., & Worek, F. (2009). Suitability of human butyrylcholinesterase as therapeutic marker and pseudo catalytic scavenger in organophosphate poisoning: a kinetic analysis. Toxicology, 259, 133-139.
8. Trovaslet-Leroy, M., Musilova, L., Renault, F., Brazzolotto, X., Misik, J., Novotny, L. et al. (2011). Organophosphate hydrolases as catalytic bioscavengers of organophosphorus nerve agents. Toxicology Letters, 206, 14-23.
9. Nachon, F., Carletti, E., Wandhammer, M., Nicolet, Y., Schopfer, L. M., Masson, P. et al. (2011). X-ray crystallographic snapshots of reaction intermediates in the G117H mutant of human butyrylcholinesterase, a nerve agent target engineered into a catalytic bioscavenger. Biochemical Journal, 434, 73-82.
10. Millard, C. B., Lockridge, O., & Broomfield, C. A. (1995). Design and expression of organophosphorus acid anhydride hydrolase activity in human butyrylcholinesterase. Biochemistry, 34, 15925-15933.
11. Lockridge, O., Blong, R. M., Masson, P., Froment, M. T., Millard, C. B., & Broomfield, C. A. (1997). A single amino acid substitution, Gly117His, confers phosphotriesterase (organophosphorus acid anhydride hydrolase) activity on human butyrylcholinesterase. Biochemistry, 36, 786-795.
12. Wang, Y., Boeck, A. T., Duysen, E. G., Van Keuren, M., Saunders, T. L., & Lockridge, 0. (2004). Resistance to organophosphorus agent toxicity in transgenic mice expressing the G117H mutant of human butyrylcholinesterase. Toxicology & Applied Pharmacology, 196, 356-366.
13. Xu, L., Huang, C. C., Huang, W. Q., Tang, W. H., Rait, A., Pirollo, K., and Chang, E. H. (2002). Systemic tumor-targeted gene delivery by anti-transferrin receptor scFv-immunoliposomes. Molecular Cancer Therapeutics, 1, 337-346.
14. Pirollo, K. F., Rait, A. S., Zhou, Q., Zhang, X-Q., Zhou, J., Kim, C-S., Benedict, W. F., and Chang, E. H. (2008). Tumor-targeting nanocomplex delivery of novel tumor suppressor RB94 chemosensitizes bladder carcinoma cells in vitro and in vivo. Clinical Cancer Research, 14, 2190-2198.
15. Rait, A. S., Pirollo, K. F., Xiang, L., and Chang, E. H. (2002). Tumor-targeting, systemically delivered ASHER-2 chemosensitizes human breast cancer xenografts irresective of HER-2 levels. Molecular Medicine, 8, 475-486.
16. Pirollo, K. F., Rait, A., Dagata, J. A., Zon, G., Hogrefe, R. I., Palchik, G., and Chang, E. H. (2007). Materializing the Potential of siRNA Via a Tumor-Targeting Nanodelivery System. Cancer Research, 67 (7), 2932-2937.
17. Hwang, S. H., Rait, A., Pirollo, K. F., Chinigo, G. M., Brown, M. L., and Chang, E. H. (2008). Tumor-targeting nanodelivery enhances the anticancer activity of novel quinazolinone analog. Molecular Cancer Therapeutics, 7(3), 1-10.
18. Freedman, M., Chang, E. H., Zhou, Q., and Pirollo, K. F. (2009): Nanodelivery of MRI contrast agent enhances sensitivity of detection of lung cancer metastases. Academic Radiology, 16, 627-637
19. Chang, E. H. (2011). Targeted Iron Oxide Nanocomplex as a Theranostic Agent for Cancer. In: Nanomedicine—Basic and Clinical Applications in Diagnostics and Therapy. (C. Alexiou, ed.), Else Kroner-Fresenius Symp. Basel, Karger, 145-153.
20. Marino, D. J. (2012). Absolute and relative organ weight trends in B6C3F1 mice. Journal of Toxicology and Environmental Health, Part A: Current Issues, 75(3), 148-169.
21. Rosenblum, K., Futter, M., Jones, M., Hulme, E. C., & Bliss, T. V. (2000). ERKI/II regulation by the muscarinic acetylcholine receptors in neurons. Journal of Neuroscience, 20, 977-985.
22. Gunnell, D., Eddleston, M., Phillips, M. R., & Konradsen, F. (2007). The global distribution of fatal pesticide self-poisoning: systematic review. BMC Public Health, 7, 357.
23. Parikh, K., Duysen, E. G., Snow, B., Jensen, N. S., Manne, V., Lockridge, O. et al. (2011). Gene-delivered butyrylcholinesterase is prophylactic against the toxicity of chemical warfare nerve agents and organophosphorus compounds. Journal of Pharmacology & Experimental Therapeutics, 337, 92-101.
24. Ledley, F. D. (1995). Nonviral gene therapy: the promise of genes as pharmaceutical products. Human Gene Therapy, 6, 1129-1144.
25. Pirollo, K. F., Xu, L., & Chang, E. H. (2000). Non-viral gene delivery for p53. Current Opinion in Molecular Therapeutics, 2, 168-175.
26. Clark, P. R., & Hersh, E. M. (1999). Cationic lipid-mediated gene transfer: current concepts. Current Opinion in Molecular Therapeutics, 1, 158-176.
27. The Journal of Gene Medicine Clinical Trials Database. Wiley. June 2012.
28. Lian, T., & Ho, R. J. (2001). Trends and developments in liposome drug delivery systems. Journal of Pharmaceutical Sciences, 90, 667-680.
29. Li, B., Duysen, E. G., Carlson, M., & Lockridge, 0. (2008). The butyrylcholinesterase knockout mouse as a model for human butyrylcholinesterase deficiency. Journal of Pharmacology & Experimental Therapeutics, 324, 1146-1154.
30. Dimov, D., Kanev, K., & Dimova, I. (2012). Correlation between butyrylcholinesterase variants and sensitivity to soman toxicity. Acta Biochimica Polonica, 59, 313-316.
31. Saxena, A., Sun, W., Hastings, N. B., Doctor, B. P., Dabisch, P. A., Hulet, S. W., Jakubowski, E. M., & Mioduszewski, R. J. Human serum butyrylcholinesterase: a bioscavenger for the protection of humans from organophosphorus exposure. RTO-MP-HFM-181. NATO/OTAN Monograph.
32. Yu, W., Pirollo, K. F., Yu, B., Rait, A., Xiang, L., Huang, W., Zhou, Q., Ertem, G., and Chang, E. H. (2004). Enhanced transfection efficiency of a systemically delivered tumor-targeting immunolipoplex by inclusion of a pH-sensitive histidylated oligolysine peptide. Nucleic Acids Research, 32, e48.
33. Karnovsky, M. J. & Roots, L. (1964). A "direct-coloring" thiocholine method for cholinesterases. Journal of Histochemistry & Cytochemistry, 12, 219-221.
34. Ellman, G. L., Courtney, K. D., Andres, V., Jr., & Feather-Stone, R. M. (1961). A new and rapid colorimetric determination of acetylcholinesterase activity. Biochemical Pharmacology, 7, 88-95.
35. Paraoanu, L. E., Mocko, J. B., Becker-Roeck, M., Smidek-Huhn, J., & Layer, P. G. (2006). Exposure to diazinon alters in vitro retinogenesis: retinospheroid morphology, development of chicken retinal cell types, and gene expression. Toxicological Sciences, 89, 314-324.
36. Kawabata, A., Kuroda, R., Nagata, N., Kawao, N., Masuko, T., Nishikawa, H. et al. (2001). In vivo evidence that protease-activated receptors 1 and 2 modulate gastrointestinal transit in the mouse. British Journal of Pharmacology, 133, 1213-1218.
37. Senzer, N., Nemunaitis, J., Nemunaitis, D., Bedell, C., Edelman, G., Barve, M., Nunan, R., Pirollo, K. F., Rait, A., and Chang, E. H. (2013). Phase I Study of a Systemically Delivered p53 Nanoparticle in Advanced Solid Tumors. Molecular Therapy (in press).

All publications, patents and patent applications mentioned in this specification are herein incorporated by reference to the same extent as if each individual publication, patent or patent application was specifically and individually indicated to be incorporated by reference.

What is claimed is:

1. A method of delivering butyrylcholinesterase (BChE) across the blood-brain barrier and also to the bloodstream of a mammal, comprising administering to the mammal a cationic liposome complex, wherein the cationic liposome complex comprises:
   (a) a cationic liposome;
   (b) an anti-transferrin receptor single chain Fv (TfRscFv) directly complexed with, but not chemically conjugated to, the cationic liposome;
   (c) a nucleic acid molecule encoding butyrylcholinesterase (BChE); and
   (d) a nucleic acid molecule encoding a polyproline rich peptide,
   wherein the TfRscFv and the cationic liposome are present at a ratio in the range of about 1:20 to about 1:40 (w:w) and the nucleic molecules are present at a ratio of about 1:5 to about 1:20 (μg nucleic acid:μg liposome).

2. The method of claim 1, wherein the cationic liposome complex is administered via a route selected from the group consisting of intranasal administration, intravenous administration, oral administration, sublingual administration, intramuscular administration, intralesional administration, intradermal administration, transdermal administration, intraocular administration, intraperitoneal administration, percutaneous administration, aerosol administration, intraorgan administration, intracereberal administration, topical administration, subcutaneous administration, endoscopic administration, slow release implant, administration via an osmotic or mechanical pump and administration via inhalation.

3. The method of claim 1, wherein the cationic liposome complex is administered via transdermal administration, intranasal administration or via inhalation.

4. The method of claim 1, wherein the cationic liposome complex is administered so as to result in an amount of BChE in the bloodstream of a human of at least 250 mg/70 kg (weight of BChE/weight of the human).

5. The method of claim 1, wherein the nucleic acid molecule encoding butyrylcholinesterase (BChE) is contained in a first plasmid associated with the cationic liposome; and the nucleic acid molecule encoding the polyproline rich peptide is contained in a second plasmid associated with the cationic liposome.

6. The method of claim 5, wherein the nucleic acid molecule encoding BChE is contained in the first plasmid construct, comprising, from 5' to 3': (a) at least one human adenovirus enhancer sequence; (b) a cytomegalovirus (CMV) promoter; (c) a multiple cloning site; (d) the nucleic acid molecule encoding BChE; and (e) an SV 40 poly A sequence, wherein the 3' end of the plasmid construct does not comprise adenovirus map units 9-16 when compared to a wild-type adenovirus.

7. The method of claim 5, wherein the nucleic acid molecule encoding the polyproline rich peptide is contained in the second plasmid construct, comprising, from 5' to 3': (a) at least one human adenovirus enhancer sequence; (b) a cytomegalovirus (CMV) promoter; (c) a multiple cloning site; (d) the nucleic acid molecule encoding the polyproline rich peptide; and (e) an SV 40 poly A sequence, wherein the 3' end of the plasmid construct does not comprise adenovirus map units 9-16 when compared to a wild-type adenovirus.

8. The method of claim 1, wherein the nucleic acid molecule encoding butyrylcholinesterase (BChE) and the nucleic acid molecule encoding the polyproline rich peptide are contained in the same plasmid associated with the cationic liposome.

9. The method of claim 8, wherein the nucleic acid molecule encoding butyrylcholinesterase (BChE) and/or the nucleic acid molecule encoding the polyproline rich peptide are contained in a plasmid, comprising one or more inserts, each insert comprising from 5' to 3': (a) at least one human adenovirus enhancer sequence; (b) a cytomegalovirus (CMV) promoter; (c) a multiple cloning site; (d) one or more nucleic acid molecules encoding the nucleic acid molecule encoding butyrylcholinesterase (BChE) and/or one or more nucleic acid molecules encoding the polyproline rich peptide; and (e) an SV 40 poly A sequence, wherein the 3' end of the plasmid construct does not comprise adenovirus map units 9-16 when compared to a wild-type adenovirus.

10. The method of claim 1, wherein the BChE is a mutant version of BChE.

11. The method of claim 10, wherein the mutant version of BChE is a G117H mutant.

12. The method of claim 1, wherein the cationic liposome comprises a mixture of one or more cationic lipids and one or more neutral or helper lipids.

13. The method of claim 12, wherein said cationic liposome comprises a mixture of dioleoyltrimethylammonium phosphate with dioleoylphosphatidylethanolamine and cholesterol; a mixture of dioleoyltrimethylammonium phosphate with cholesterol, a mixture of dimethyldioctadecylammonium bromide with dioleoylphosphatidylethanolamine and cholesterol, a mixture of dimethyldioctadecylammonium bromide with dioleoylphosphatidylethanolamine, a mixture of dimethyldioctadecylammonium bromide with cholesterol, or a mixture of dioleoyltrimethylammonium phosphate with dioleoylphosphatidylethanolamine.

14. The method of claim 1, wherein the nucleic acid molecules are present at a molar ratio of about 10:1 to about 1:10 (moles nucleic acid molecule encoding butyrylcholinesterase (BChE):moles nucleic acid molecule encoding the polyproline rich peptide).

15. The method of claim 14, wherein the nucleic acid molecules are present at a molar ratio of about 5:1 to about 1:5 (moles nucleic acid molecule encoding butyrylcholinesterase (BChE):moles nucleic acid molecule encoding the polyproline rich peptide).

16. The method of claim 14, wherein the nucleic acid molecules are present at a molar ratio of about 4:1 (moles nucleic acid molecule encoding butyrylcholinesterase (BChE):moles nucleic acid molecule encoding the polyproline rich peptide), or wherein the nucleic acid molecules are present at a molar ratio of about 2:1 (moles nucleic acid molecule encoding butyrylcholinesterase (BChE):moles nucleic acid molecule encoding the polyproline rich peptide).

17. The method of claim 14, wherein the nucleic acid molecules are present at a molar ratio of about 1:1 (moles nucleic acid molecule encoding butyrylcholinesterase (BChE):moles nucleic acid molecule encoding the polyproline rich peptide).

18. The method of claim 1, wherein the nucleic acid molecules are encapsulated within the cationic liposome, contained within a hydrocarbon chain region of the cationic liposome, associated with an inner or outer monolayer, or any combination thereof.

19. A method of delivering butyrylcholinesterase (BChE) across the blood-brain barrier and to the bloodstream of a human, comprising administering intranasally or via aerosol inhalation to the mammal a cationic liposome complex, wherein the cationic liposome complex comprises:
   (a) a cationic liposome;
   (b) an anti-transferrin receptor single chain Fv (TfRscFv) directly complexed with, but not chemically conjugated to, the cationic liposome;
   (c) a nucleic acid molecule encoding butyrylcholinesterase (BChE) associated with the cationic liposome; and
   (d) a nucleic acid molecule encoding a polyproline rich peptide associated with the cationic liposome,
   wherein the TfRscFv and the cationic liposome are present at a ratio in the range of about 1:20 to about 1:40 (w:w) and the nucleic molecules are present at a ratio of about 1:5 to about 1:20 (µg nucleic acid:µg liposome),
   wherein the nucleic acid molecules are present at a molar ratio of about 10:1 to about 1:10 (moles nucleic acid molecule encoding butyrylcholinesterase (BChE): moles nucleic acid molecule encoding a polyproline rich peptide),
   and wherein the complex is administered so as to result in an amount of BChE in the bloodstream of the human of at least 250 mg/70 kg (weight of BChE/weight of the human).

20. The method of claim 19, wherein the BChE is a mutant version of BChE; and wherein the cationic liposome comprises a mixture of dioleoyltrimethylammonium phosphate with dioleoylphosphatidylethanolamine and cholesterol; a mixture of dioleoyltrimethylammonium phosphate with cholesterol, a mixture of dimethyldioctadecylammonium bromide with dioleoylphosphatidylethanolamine and cholesterol, a mixture of dimethyldioctadecylammonium bromide with dioleoylphosphatidylethanolamine, a mixture of dimethyldioctadecylammonium bromide with cholesterol, or a mixture of dioleoyltrimethylammonium phosphate with dioleoylphosphatidylethanolamine.

\* \* \* \* \*

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Histidylated residue
<220> FEATURE:
<221> NAME/KEY: MOD_RES
<222> LOCATION: (6)..(6)
<223> OTHER INFORMATION: Histidylated residue
<220> FEATURE:
<221> NAME/KEY: MOD_RES
<222> LOCATION: (10)..(10)
<223> OTHER INFORMATION: Histidylated residue
<220> FEATURE:
<221> NAME/KEY: MOD_RES
<222> LOCATION: (14)..(14)
<223> OTHER INFORMATION: Histidylated residue
<220> FEATURE:
<221> NAME/KEY: MOD_RES
<222> LOCATION: (18)..(18)
<223> OTHER INFORMATION: Histidylated residue
<220> FEATURE:
<221> NAME/KEY: MOD_RES
<222> LOCATION: (22)..(22)
<223> OTHER INFORMATION: Histidylated residue

<400> SEQUENCE: 1

Lys Lys Lys Lys Lys Lys Lys Lys Lys Lys Lys Lys Lys Lys Lys
1               5                   10                  15

Lys Lys Lys Lys Lys Lys Lys Lys Cys
                20                  25
```